United States Patent
Kayyali et al.

(10) Patent No.: US 11,484,255 B1
(45) Date of Patent: *Nov. 1, 2022

(54) METHOD AND DEVICE FOR SLEEP ANALYSIS

(71) Applicant: Cleveland Medical Devices Inc., Cleveland, OH (US)

(72) Inventors: Hani Kayyali, Shaker Heights, OH (US); Craig A. Frederick, Solon, OH (US); Robert N. Schmidt, Ft. Myers, FL (US); Brian M. Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,104

(22) Filed: Jun. 10, 2022

Related U.S. Application Data

(63) Continuation of application No. 17/704,085, filed on Mar. 25, 2022, now Pat. No. 11,395,623, which is a continuation of application No. 17/515,866, filed on Nov. 1, 2021, now Pat. No. 11,317,856, which is a continuation of application No. 16/599,330, filed on Oct. 11, 2019, now Pat. No. 11,202,603, which is a continuation of application No. 16/014,002, filed on Jun. 21, 2018, now Pat. No. 10,478,118, which is a continuation of application No. 14/883,687, filed on Oct. 15, 2015, now Pat. No. 10,028,698, which is a continuation of application No. 11/811,157, filed on Jun. 8, 2007, now Pat. No. 9,202,008.

(51) Int. Cl.
*A61B 5/00* (2006.01)
*A61B 5/1455* (2006.01)
*A61B 5/087* (2006.01)
*A61B 5/369* (2021.01)

(52) U.S. Cl.
CPC .......... *A61B 5/4815* (2013.01); *A61B 5/0006* (2013.01); *A61B 5/0022* (2013.01); *A61B 5/087* (2013.01); *A61B 5/14552* (2013.01); *A61B 5/369* (2021.01); *A61B 5/486* (2013.01); *A61B 5/6831* (2013.01); *A61B 5/7282* (2013.01); *A61B 2560/0214* (2013.01); *A61B 2560/0475* (2013.01); *A61B 2562/0219* (2013.01)

(58) Field of Classification Search
None
See application file for complete search history.

(56) References Cited

U.S. PATENT DOCUMENTS 5,842,978 A * 12/1998 Levy .................... A61B 5/0006
 348/E7.086
5,953,713 A * 9/1999 Behbehani .......... A61M 16/026
 706/15

(Continued)

*Primary Examiner* — Shirley X Jian
(74) *Attorney, Agent, or Firm* — Brian Kolkowski

(57) ABSTRACT

The various embodiments of the method of the present invention include a method to improving or expanding the capacity of a sleep analysis unit or laboratory, a method sleep analysis testing a patient admitted for diagnosis or treatment of another primary medical condition while being treated or diagnosed for that condition, a method of sleep analysis testing a patient that cannot be easily moved or treated in a sleep analysis unit or laboratory and other like methods.

20 Claims, 10 Drawing Sheets

(56) References Cited

U.S. PATENT DOCUMENTS

| | | | | |
|---|---|---|---|---|
| 5,974,340 A * | 10/1999 | Kadhiresan | A61N 1/36542 | 607/18 |
| 6,306,088 B1 * | 10/2001 | Krausman | A61B 5/02055 | 600/534 |
| 6,397,845 B1 * | 6/2002 | Burton | A61M 16/0051 | 128/204.26 |
| 6,454,708 B1 * | 9/2002 | Ferguson | G16H 10/65 | 128/903 |
| 6,551,252 B2 * | 4/2003 | Sackner | A61B 5/002 | 600/509 |
| 6,811,538 B2 * | 11/2004 | Westbrook | A61B 5/0205 | 600/323 |
| 6,997,882 B1 * | 2/2006 | Parker | A61B 5/08 | 600/595 |
| 7,081,095 B2 * | 7/2006 | Lynn | A61B 5/087 | 600/300 |
| 7,267,652 B2 * | 9/2007 | Coyle | A61B 5/725 | 600/529 |
| 7,299,088 B1 * | 11/2007 | Thakor | G06K 9/00523 | 600/544 |
| 7,382,247 B2 * | 6/2008 | Welch | G08B 21/0446 | 340/8.1 |
| 7,460,903 B2 * | 12/2008 | Pineda | A61N 2/006 | 600/545 |
| 7,502,643 B2 * | 3/2009 | Farringdon | A61B 5/316 | 600/509 |
| 7,515,044 B2 * | 4/2009 | Welch | A61B 5/002 | 340/286.07 |
| 7,593,767 B1 * | 9/2009 | Modarres | A61B 5/4818 | 600/534 |
| 7,670,295 B2 * | 3/2010 | Sackner | A61B 5/6805 | 600/595 |
| 7,774,052 B2 * | 8/2010 | Burton | A61B 5/11 | 600/545 |
| 7,942,824 B1 * | 5/2011 | Kayyali | A61M 16/0003 | 128/204.26 |
| 8,172,766 B1 * | 5/2012 | Kayyali | A61B 5/02055 | 128/204.26 |
| 8,545,416 B1 * | 10/2013 | Kayyali | A61B 5/0205 | 128/204.26 |
| 8,639,354 B2 * | 1/2014 | Bolea | A61N 1/0558 | 607/118 |
| 8,679,012 B1 * | 3/2014 | Kayyali | A61B 5/1455 | 600/301 |
| 9,202,008 B1 * | 12/2015 | Frederick | A61B 5/0022 | |
| 9,730,632 B1 * | 8/2017 | Kayyali | A61B 5/0809 | |
| 2002/0032386 A1 * | 3/2002 | Sackner | A61B 5/6822 | 600/509 |
| 2002/0165462 A1 * | 11/2002 | Westbrook | A61B 5/7275 | 600/529 |
| 2003/0000522 A1 * | 1/2003 | Lynn | A61B 5/145 | 128/200.24 |
| 2003/0135127 A1 * | 7/2003 | Sackner | A61B 5/0205 | 600/536 |
| 2004/0138578 A1 * | 7/2004 | Pineda | A61N 1/006 | 600/544 |
| 2004/0138719 A1 * | 7/2004 | Cho | A61N 1/3601 | 607/42 |
| 2004/0193068 A1 * | 9/2004 | Burton | A61B 5/369 | 600/595 |
| 2004/0244807 A1 * | 12/2004 | Sun | A61B 5/0002 | 600/26 |
| 2005/0113703 A1 * | 5/2005 | Farringdon | A61B 5/25 | 600/509 |
| 2005/0121033 A1 * | 6/2005 | Starr | A61M 16/06 | 128/204.23 |
| 2005/0240087 A1 * | 10/2005 | Keenan | A61B 5/6804 | 600/509 |
| 2006/0084877 A1 * | 4/2006 | Ujhazy | A61B 5/0826 | 600/483 |
| 2007/0032733 A1 * | 2/2007 | Burton | A61B 5/7264 | 600/509 |
| 2008/0306348 A1 * | 12/2008 | Kuo | A61B 5/0006 | 600/300 |
| 2010/0076333 A9 * | 3/2010 | Burton | A61B 5/16 | 600/595 |
| 2010/0204550 A1 * | 8/2010 | Heneghan | A61B 5/411 | 600/529 |
| 2012/0022626 A1 * | 1/2012 | Bolea | A61N 1/37229 | 607/118 |
| 2015/0148624 A1 * | 5/2015 | Benaron | A61B 5/085 | 600/479 |
| 2015/0148625 A1 * | 5/2015 | Benaron | A61B 5/14552 | 600/479 |
| 2015/0164375 A1 * | 6/2015 | Schindhelm | G08B 21/02 | 600/534 |

* cited by examiner

METHOD AND DEVICE FOR SLEEP ANALYSIS

CROSS-REFERENCE TO RELATED APPLICATIONS

This application claims priority as a continuation of U.S. patent application Ser. No. 17/704,085, which was filed on Mar. 25, 2022, and which is a continuation of U.S. patent application Ser. No. 17/515,866, which was filed on Nov. 1, 2021, issued as U.S. Pat. No. 11,317,856 on May 3, 2022, and which is a continuation of U.S. patent application Ser. No. 16/599,330, which was filed on Oct. 11, 2019, issued as U.S. Pat. No. 11,202,603 on Dec. 21, 2021, and which is a continuation of U.S. patent application Ser. No. 16/014,002, which was filed on Jun. 21, 2018 and issued as U.S. Pat. No. 10,478,118 on Nov. 19, 2019, and which is a continuation of U.S. patent application Ser. No. 14/883,687, which was filed on Oct. 15, 2015 and issued as U.S. Pat. No. 10,028,698 on Jul. 24, 2018, and which is a continuation of U.S. patent application Ser. No. 11/811,157, which was filed on Jun. 8, 2007 and issued as U.S. Pat. No. 9,202,008 on Dec. 1, 2015. The specifications and drawings of each of the above patents and applications are hereby incorporated by reference in their entirety.

LICENSE RIGHTS FOR FEDERALLY-SPONSORED RESEARCH

The U.S. Government has a paid-up license in this invention and the right in limited circumstances to require the patent owner to license others on reasonable terms provided for by the terms of grant numbers 2R44NS042451-04 and 5R44NS042451-03 awarded by the National Institutes of Health.

BACKGROUND OF THE INVENTION

Nearly one in seven people in the United States suffer from some type of chronic sleep disorder, and only 50% of people are estimated to get the recommended seven to eight hours of sleep each night. It is further estimated that sleep deprivation and its associated medical and social costs (loss of productivity, industrial accidents, etc.) exceed $150 billion per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Primary sleep disorders affect approximately 50 million Americans of all ages and include narcolepsy, restless legs/periodic leg movement, insomnia, and most commonly, obstructive sleep apnea (OSA). OSA's prevalence in society is comparable with diabetes, asthma, and the lifetime risk of colon cancer. OSA is grossly under diagnosed; an estimated 80-90% of persons afflicted have not received a clinical diagnosis. Some medical conditions have been associated with increased risk for sleep disorders, specifically sleep-related breathing disorders. Such conditions include cardiovascular disease such as hypertension, stroke, and congestive heart failure. Evidence indicates that treatment of the sleep-related breathing disorder can improve cardiac function in these patients. Similarly, evidence indicates sleep-related breathing disorders can increase the prevalence of nocturnal cardiac arrhythmia development.

Sleeping disorders are currently diagnosed by two general methods. Subjective methods, such as the Epworth and Standford Sleepiness Scale, generally involve questionnaires that require patients to answer a series of qualitative questions regarding their sleepiness during the day. With these subjective methods, however, it is found that the patients usually underestimate their level of sleepiness or they deliberately falsify their responses because of their concern regarding punitive action or as an effort to obtain restricted stimulant medication. The second group of methods uses physiological evaluations, such as all-night polysomnography to evaluate a patient's sleep architecture (e.g., obtaining respiratory disturbance index to diagnose sleep apnea). A polysomnogram (PSG) can also be followed by an all-day test such as the Multiple Sleep Latency Test (MSLT) or its modified version, the Maintenance of Wakefulness Test (MWT). The PSG typically requires patients to spend the night in a sleep laboratory connected to multiple sensors while they attempt to sleep.

Sleep laboratory studies require the patient to physically go to the sleep lab to be tested. These labs typically have a small number of sleeping rooms containing all the necessary sleep study equipment. The equipment from each room many times is wired to a central monitoring room where a sleep technician collects and analyzes data from several subjects. Due to the limited capacity and a high volume of patients requiring sleep studies, many labs have unacceptable waiting lists. Additionally, many patients requiring sleep studies have related medical conditions, such as severe cardiovascular disease, or are immobile making travel to a sleep lab difficult. As a result, many patients must wait for an available appointment or improved health before a laboratory-based sleep study is possible. This delay in diagnosing the patient's sleep disorder leads to a delay in treatment and an increased risk of developing a related medical condition.

Current methods attempting to conduct a sleep study at the patient's location have proved unsuccessful. Patients who are already ill or hospitalized cannot travel to a sleep lab, nor can a sleep test be conducted in an inpatient hospital room. Standard, and even specialized, hospital rooms are not equipped to conduct a sleep study. Facilities are not frequently retrofitted with sleep study equipment due to the huge expense involved, particularly for limited use. Further, hospital rooms are crowded with other equipment, which makes adding bulky sleep study carts infeasible. Similarly, few hospitals have space near patient rooms available for use as a monitoring room.

To address some of these concerns, methods have been developed to conduct unattended studies. An unattended sleep test does not require the step of transmitting the data to a monitoring location. These methods have relied on equipment incapable of transmitting data during the sleep study, creating the unattended test. Such unattended tests, however, are plagued with signal failure. In one study involving unattended PSG, data from over 23% of the patients were unusable due to missing channels, even though a technician called the PSG recording device every 30 minutes to check the quality of the recordings. Further, unattended tests do not resolve the problem of fitting a sleep cart into a crowded patient room.

None of the current methods for conducting a sleep study outside a sleep lab allow transmission of the collected data during the test. All of the current methods require the PSG data to be stored during the test and read only after the test has been completed. As such, the data cannot be periodically or continuously checked for adequacy. Even if the data were periodically evaluated, the current methods do not use a step of allowing a remote monitor to communicate with the subject to correct any sensor/signal problems. The current methods also do not include live video feeds that enable a remote monitor to visualize the subject during the sleep test. Moreover, the current methods make it extremely difficult to conduct a full polysonnagram sleep study outside a sleep lab have enabled the entire sleep system to fit inside a crowded hospital room.

It is therefore an object of the present invention to provide a method of conducting a sleep analysis outside a sleep lab wherein the data is transmitted at substantially the same time it that is collected or created. It is another object of the present invention to provide a method of conducting a sleep analysis outside the sleep lab that is remotely attended. It is another objective of the present invention to provide a method of conducting a sleep analysis outside the sleep lab on subjects who are already patients in a hospital room. It is still another objective of the present invention to provide a method of conducting a sleep analysis with a small, lightweight data acquisition system.

SUMMARY OF THE INVENTION

The present invention provides a method of conducting a sleep analysis by collecting physiologic and kinetic data from a subject with a wireless data acquisition system, in a non-traditional location such as a hospital room, nursing home, a satellite hospital, hotel, and the like. The sleep analysis, including clinical and research sleep studies, can be used in the diagnosis of sleeping disorders and other diseases or conditions with sleep signatures, such as Parkinson's, epilepsy, chronic heart failure, chronic obstructive pulmonary disorder, or other neurological, cardiac, pulmonary, or muscular disorders.

The various embodiments of the method of the present invention include a method to improving or expanding the capacity of a sleep analysis unit or laboratory, a method sleep analysis testing a patient admitted for diagnosis or treatment of another primary medical condition while being treated or diagnosed for that condition, a method of sleep analysis testing a patient that cannot be easily moved or treated in a sleep analysis unit or laboratory and other like methods.

The various embodiments of the present invention include a number of steps that enhance these methods over other methods presently used. These features available in various embodiments of the present invention may include, but are not necessarily limited to: a step for hooking up the patient with the necessary sensors at a remote location, a step for collecting multiple channels of data to evaluate a number of physiological, kinetic, and environmental features of the subject and sleeping location; a step for including a subject's body motion; a step for using removable memory for data buffering and storage; a step for movement artifact correction using video; a step for transmitting data wirelessly to a remote processing or monitoring station after a manual or automatic radio frequency (RF) sweep; a step for remotely checking the data for adequacy; a step for remotely monitoring the subject via streaming data and audio/video for the duration of the test; a step for communicating with the subject during the test; and a step for adjusting electrodes and other sensors during the test.

The software used in various steps of the present invention allows the patient data acquisition system to perform a number of operations that other systems cannot accomplish with the same type of hardware. The use of software filtering allows determination of airflow, tidal volume, ventilation rate, and snore detection from a single pressure transducer. The use of software also makes many of the video-related features possible. Software is used to synchronize video with the other signals for display. Software is also used to remove data artifacts created by subject movement. The software corrects motion artifacts by using data acquired from accelerometers and video.

The present invention preferably contains the step of wirelessly transmitting data from the sensors for the sleep analysis at substantially the same time as it is collected. The patient wireless acquisition system of the present invention is preferably small and compact resulting in ease of use and improved patient mobility by eliminating the need to tether the patient.

The present invention may also include the step of transmitting data via a wired network such as a dial-up modem, cellular networks, digital subscriber lines (DSL), cable broadband, fiber-optic lines, satellite communications, direct radio, infra-red links, and the like. The data can be transmitted once, at multiple points during the test, or continuously. With continuous data transmission, the sleep test can be remotely monitored from anywhere around the world. The data furthermore may be monitored by multiple viewing stations by methods including but not limited to serial retransmission from one station to another, or simultaneous transmission by 3-way or conference calling, broadcasting or the like. The data from the acquisition system is available for remote monitoring in real time, it can be saved and scored later, or may be quantitatively analyzed and scored (even automatically) and then viewed. With automatic or computer-assisted scoring, the software can alert a individual performing remote monitoring when a physiological event (such as a drop in oxygen saturation) or a technological event (such as an electrode becoming disconnected) occurs.

Various embodiments of the present invention include the step of applying at least two sensors to the subject. The sensors can be applied by a sleep technician, a clinician, a nurse or the like, at any location, preferably however, either at the facility which is being used to expand the capacity of the sleep unit or laboratory, the facility to which the patient was admitted for treatment of a primary medical condition, other than a sleeping disorder, or at the location of the immobile patient such as a nursing home, extended care facility, or the like. The method of the present invention further allows for hospital in-patient sleep analysis where the patient is admitted for diagnosis or treatment to a general medical or surgical unit, to a cardiac unit, to a respiratory unit, gastrointestinal unit, neurological unit, trauma unit, intensive care unit, maternity unit, pediatric unit, oncology unit, urology unit, psychiatric unit, hematology unit, infectious disease unit, orthopedic unit, ear nose and throat unit, dermatology unit, or the like In one embodiment, the present invention includes a method of expanding the capacity of a sleep analysis lab or unit comprising the steps of applying at least two sensors to a patient located in a facility remote to a sleep analysis unit or lab; connecting the at least two sensors to a wireless data acquisition system; collecting data from the patient located in the remote facility while the patient is attempting to sleep; wirelessly transmitting the data at substantially the same time as it is collected to the sleep analysis unit or lab or to a database accessible to individuals from the sleep analysis unit or lab; and analysis of the data by individuals from the sleep analysis unit or lab to determine whether the patient suffers from a sleep disorder.

In another embodiment, the present invention includes a method of sleep analysis or diagnosis on a patient admitted for diagnosis or treatment for other primary medical conditions comprising the steps of admitting a patient for diagnosis or treatment of a primary medical condition, other than a sleeping disorder, to a hospital room, other than one used primarily for sleep diagnosis or treatment; suspecting that the patient may have a related or underlying sleep disorder; applying at least two sensors to the patient; connecting the at least two sensors to a wireless data acquisition system; collecting data from the patient located in the hospital room while the patient is attempting to sleep; wirelessly transmitting the data at substantially the same time as it is collected to a sleep analysis unit or lab or to a database accessible to individuals from the sleep analysis unit or lab; and analysis of the data by individuals from the sleep analysis unit or lab to determine whether the patient suffers from a sleep disorder.

In still another embodiment, the present invention includes a method of sleep analysis or diagnosis on a patient who cannot be moved to a sleep unit or lab, comprising the steps of suspecting that a patient may have a related or underlying sleep disorder; applying at least two sensors to the patient; connecting the at least two sensors to a wireless data acquisition system; collecting data from the patient at a location that is not a sleep unit or lab while the patient is attempting to sleep; wirelessly transmitting the data at substantially the same time as it is collected to a sleep analysis unit or lab or to a database accessible to individuals from the sleep analysis unit or lab; and analysis of the data by individuals from the sleep analysis unit or lab to determine whether the patient suffers from a sleep disorder.

Additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1:
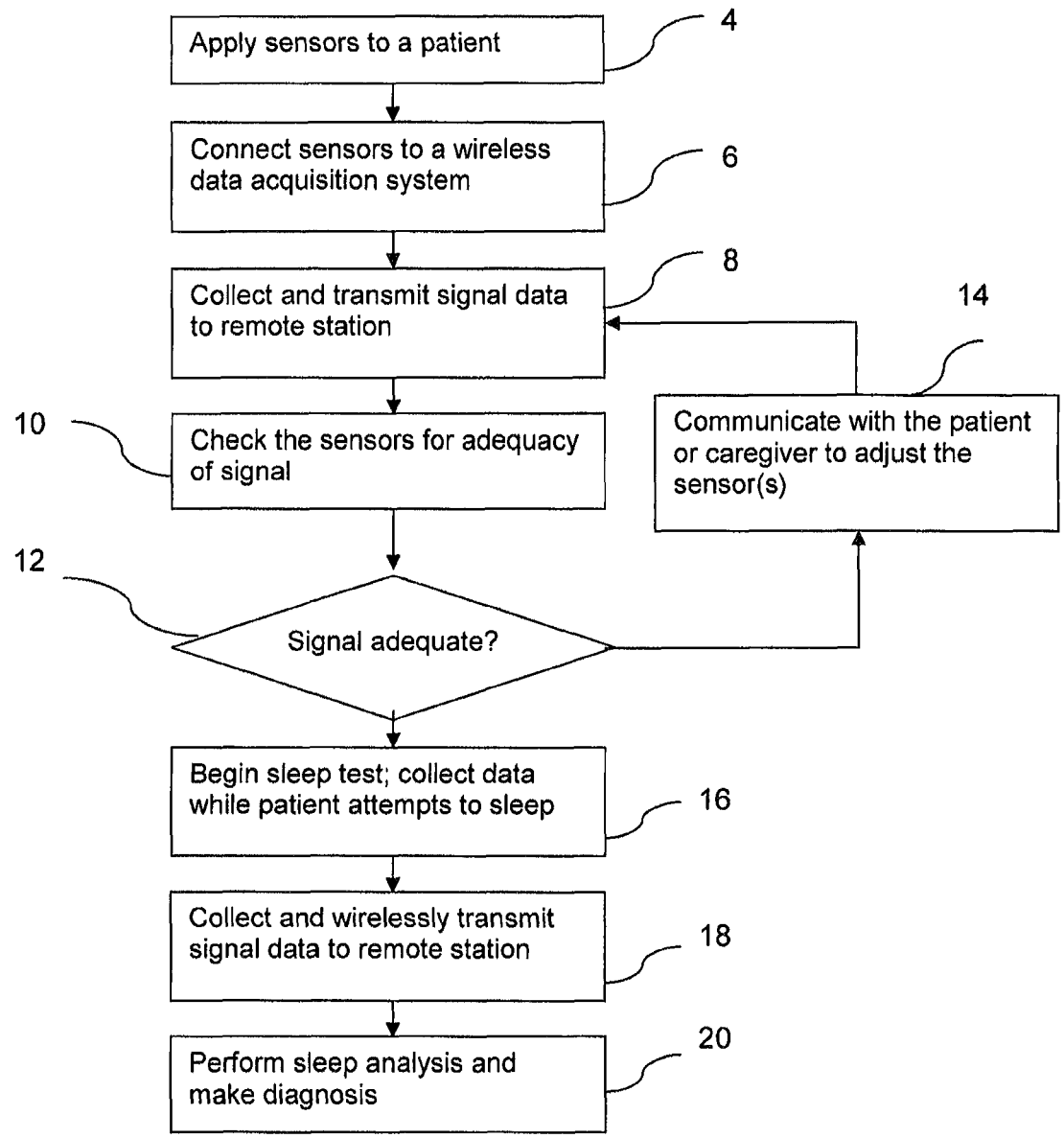
FIG. 1 Block diagram of one embodiment of the present invention including showing the steps of checking the adequacy of signals and communicating with the subject.

The present invention is related to a method of inpatient and remote sleep and signal analysis. The present invention is further related to the devices used in executing the method. The present invention includes various embodiments of a method of inpatient and remote sleep analysis. These embodiments include but are not limited to one or more of the following steps.

Various embodiments of the present invention include a step for determining whether the subject being analyzed for a sleep disorder maintained a normal sleeping pattern prior to the analysis. This step can be performed or accomplished a number of ways. In the simplest form, the subject or patient can be questioned regarding his or her previous sleep patterns. In a somewhat more complex form the subject can be requested to fill out a questionnaire, which then can be graded to determine whether his or her previous sleep patterns where normal (or appeared normal). In an even more complex form the subject might undergo all night polysomnography to evaluate the subject's sleep architecture (e.g., obtaining respiratory disturbance index to diagnose sleep apnea). One of the objectives of this step is to ensure that the results of the subject's or patient's brain wave analysis are not the result of or affected by the subject's or patient's previous environmental factors i.e., intentional lack of sleep, etc. It is clear that there are numerous ways beyond those examples previously mentioned of determining whether the subject being analyzed maintained or thought they were maintaining a normal sleeping pattern prior to analysis, therefore the examples given above are included as exemplary rather than as a limitation, and those ways of determining whether the subject maintained or thought they were maintaining a normal sleeping pattern known to those skilled in the art are considered to be included in the present invention.

Various embodiments of the present invention include the step of conducting an inpatient or remote sleep analysis that is attended from a remote location. Such remote attendance can be accomplished by an individual in a remote location (a remote monitor) periodically or continuously viewing the data transmitted from the patient data acquisition system, including signals from the sensors applied to the subject, signals from the environmental sensors, and a pre-processed signal or signals based at least in part on at least one of the sensors. Preferably, the data includes a video channel. Preferably, the remote monitor is capable of communicating with the subject or patient, their assistant, or another individual near the subject or patient. Such communication allows the remote monitor to provide instructions to the subject or patient, their assistant, or other individual near the subject or patient, for example, to adjust a sensor, close window blinds, remove a source of noise, or wake the subject. More preferably, the remote monitor is capable of two-way communication with the subject, subject's assistant, or other individual near the subject. Such communication allows the subject, subject's assistant, or other individual close to the subject to ask the remote monitor questions, for example, to clarify instructions. In many of the settings this other individual may be a nurse or trained technician at the hospital, nursing home or skilled medical facility. In other settings, it can be any other individual trained in the placement and hookup of the sensors.

Various embodiments of the present invention include the step of applying at least two sensors to the subject or patient. The sensors can be applied at any location. Preferably, the sensors are applied at the facility such as the hospital where the patient is staying, and most preferably right in the patient's room. Care needs to be given when applying these sensors so as to not disturb or interfere with other diagnostic equipment, treatment devices or sensors on or in the vicinity of the patient. For example, in an intensive care unit or cardiac unit the patient may be monitored by EKG and have three or more leads. Care must be taken not to interfere or disturb the electrodes or the signal received. In addition, this method also provides for a step in sharing common sensors. This step could include routing the data from these sensors through the patient data acquisition system or the data can be combined with the other data run through the data acquisition system down stream. For example, both the data from the patient data acquisition system and EKG might be combined and synched for time in the database, and this combined data used to make the sleep diagnosis or analysis. Similarly, the sensors can be applied by a variety of individuals, including but not limited to a physician, nurse, sleep technician, or other healthcare professional. Although not as preferable, the sensors could be applied by the patient or subject, or the patient's or subject's spouse, friend, roommate, or other individual capable of attaching the various sensors. More preferably, the sensors could be applied by the subject or the subject's spouse, friend, roommate, or other individual capable of attaching the various sensors with guidance and instruction. Such guidance and instruction can include static information such as pamphlets, audio recordings (on cassettes, compact discs, and the like), video recordings (on videocassettes, digital video discs, and the like), websites, and the like, as well as dynamic information such as direct real-time communication via telephone, cell phone, videoconference, and the like.

The sensors that are used with various embodiments of the present invention are described herein but can also be any of those known to those skilled in the art for the applications of this method. The collected physiological, kinetic, and environmental signals can be obtained by any method known in the art. Preferably, those sensors include, but are not limited, to wet or dry electrodes, photodetectors, accelerometers, pneumotachometers, strain gauges, thermal sensors, pH sensors, chemical sensors, gas sensors (such as oxygen and carbon dioxide sensors), transducers, piezo sensors, magnetometers, pressure sensors, static charge-sensitive beds, microphones, audio monitors, video monitors, and the like. The invention is envisioned to include those sensors subsequently developed by those skilled in the art to detect these types of signals. For example, the sensors can be magnetic sensors. Because electro-physiological signals are, in general, electrical currents that produce associated magnetic fields, the present invention further anticipates methods of sensing those magnetic fields to acquire the signal. For example, new magnetic sensors could collect brain wave signals similar to those that can be obtained through a traditional electrode applied to the subject's scalp.

Various embodiments of the present invention include a step for applying sensors to the subject. This step can be performed or accomplished in a number of ways. In the simplest form, two sensors are applied to the subject to measure a single channel of physiologic or kinetic data. In a somewhat more complex form, multiple sensors are applied to the subject to collect data sufficient for a full PSG test. The preferred set of sensors includes sensors for two EEG channels, two EOG channels, one chin EMG channel, one nasal airflow channel, one oral airflow channel, one ECG channel, one thoracic respiratory effort channel, one abdominal respiratory effort channel, one pulse oximetry channel, and one shin or leg EMG channel. More preferably, the full set of PSG sensors is augmented with at least one channel of body position (ex., an accelerometer), one channel of video, and optionally one channel of audio. In an even more complex form, many sensors are applied to the subject to collect full PSG data as well as additional physiological, kinetic, and environmental data. For example, additional EEG electrodes may be applied to the subject to rule out seizure disorders, an esophageal pH sensor may be used to detect acid reflux, and a hygrometer or photometer may be used to detect ambient humidity or light, respectively.

Electro-physiological signals such as EEG, ECG, EMG, EOG, electroneurogram (ENG), electroretinogram (ERG), and the like can be collected via electrodes placed at one or several relevant locations on the subject's body. For example when measuring brain wave or EEG signals, electrodes may be placed at one or several locations on the subject's scalp. In order to obtain a good electro-physiological signal, it is desirable to have low impedances for the electrodes. Typical electrodes placed on the skin may have an impedance in the range of from 5 to 10 k$\Omega$. It is in generally desirable to reduce such impedance levels to below 2 k$\Omega$. A conductive paste or gel may be applied to the electrode to create a connection with an impedance below 2 k$\Omega$. Alternatively or in conjunction with the conductive gel, a subject's skin may be mechanically abraded, the electrode may be amplified, or a dry electrode may be used. Dry physiological recording electrodes of the type described in U.S. Pat. No. 7,032,301 are herein incorporated by reference. Dry electrodes are advantageous because they use no gel that can dry out, skin abrasion or cleaning is unnecessary, and the electrode can be applied in hairy areas such as the scalp. Additionally if electrodes are used as the sensors, preferably at least two electrodes are used for each channel of data—one signal electrode and one reference electrode. Optionally, a single reference electrode may be used for more than one channel.

When electrodes are used to collect EEG or brain wave signals, common locations for the electrodes include frontal (F), parietal (P), mastoid process (A), central (C), and occipital (O). Preferably for the present invention, when electrodes are used to collect EEG or brain wave data, at least one electrode is placed in the occipital position and referenced against an electrode placed on the mastoid process (A). More preferably, when electrodes are used to collect EEG or brain wave data, electrodes are placed to obtain a second channel of data from the central location. If further EEG or brain wave signal channels are desired, the number of electrodes required will depend on whether separate reference electrodes or a single reference electrode is used.

If electrodes are used to collect cardiac signals using an ECG, they may be placed at specific points on the subject's body. The ECG is used to measure the rate and regularity of heartbeats, determine the size and position of the heart chambers assess any damage to the heart, and diagnose sleeping disorders. An ECG is important as a tool to detect the cardiac abnormalities that can be associated with respiratory-related disorders.

As the heart undergoes depolarization and repolarization, electrical currents spread throughout the body because the body acts as a volume conductor. The electrical currents generated by the heart are commonly measured by an array of twelve electrodes placed on the arms, legs, and chest. Although a full ECG test typically involves twelve electrodes, only two are required for many tests such as a sleep study. When electrodes are used to collect ECG with the present invention, preferably only two electrodes are used. When two electrodes are used to collect ECG, preferably one is placed on the subject's left-hand ribcage under the armpit, and the other preferably on the right-hand shoulder near the clavicle bone. Optionally, a full set of twelve ECG electrodes may be used, such as if the subject is suspected to have a cardiac disorder. The specific location of each electrode on a subject's body is well known to those skilled in the art and varies between both individuals and types of subjects. If electrodes are used to collect ECG, preferably the electrode leads are connected to a device contained in the signal processing module of the patient data acquisition system used in the present invention that measures potential differences between selected electrodes to produce ECG tracings.

The two basic types of ECG leads are bipolar and unipolar. Bipolar leads (standard limb leads) have a single positive and a single negative electrode between which electrical potentials are measured. Unipolar leads (augmented leads and chest leads) have a single positive recording electrode and use a combination of the other electrodes to serve as a composite negative electrode. Either type of lead is acceptable for collecting ECG signals in the present invention.

Other sensors can be used to measure various parameters of a subject's respirations. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices also preferably measure nasal pressure, respiratory inductance plethysmography, thoracic impedance, expired carbon dioxide, tracheal sound, snore sound, blood pressure and the like. Measurement of respiratory effort is preferably measured by a respiration belt, esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer, or other sensors that can indirectly measure a subject's respirations and the variability of respirations by providing a signal that correlates to the thoracic/abdominal expansion/contractions of the subject's thoracic/abdominal cavity. If respiration belts are used, they may be placed at one or several locations on the subject's torso or in any other manner known to those skilled in the art. Preferably, when respiration belts are used, they are positioned below the axilla and/or at the level of the umbilicus to measure rib cage and abdominal excursions. More preferably, at least two belts are used, with one positioned at the axilla and the other at the umbilicus.

Another example of a sensor or method for measuring respirations either directly or indirectly is a nasal cannula or a facemask used to measure the subject's respiratory airflow. Nasal or oral airflow can be measured quantitatively and directly with a pneumotachograph consisting of a pressure transducer connected to either a standard oxygen nasal cannula placed in the nose or a facemask over the subject's mouth and nose. Airflow can be estimated by measuring nasal or oral airway pressure that decreases during inspiration and increases during expiration. Inspiration and expiration produce fluctuations on the pressure transducer's signal that is proportional to airflow. A single pressure transducer can be used to measure the combined oral and nasal airflow. Alternatively, the oral and nasal components of these measurements can be acquired directly through the use of at least two pressure transducers, one transducer for each component. Preferably, the pressure transducer(s) are internal to the interface box. If two transducers are used for nasal and oral measurements, preferably each has a separate air port into the interface box.

Software filtering can obtain "snore signals" from a single pressure transducer signal by extracting the high frequency portion of the transducer signal. This method eliminates the need for a separate sensor, such as a microphone or another transducer, and also reduces the system resources required to detect both snore and airflow. A modified nasal cannula or facemask connected to a carbon dioxide or oxygen sensor may be used to measure respective concentrations of these gases. In addition, a variety of other sensors can be connected with either a nasal cannula or facemask to measure a subject's respirations directly or indirectly.

Still another example of a sensor or method of directly or indirectly measuring respirations of the subject is a pulse oximeter. The pulse oximeter can measure the oxygenation of the subject's blood by producing a source of light at two wavelengths (650 nm and 905, 910, or 940 nm). Hemoglobin partially absorbs the light by amounts that differ depending on whether it is saturated or desaturated with oxygen. Calculating the absorption at the two wavelengths leads to an estimate of the proportion of oxygenated hemoglobin. Preferably, pulse oximeters are placed on a subject's earlobe or fingertip. More preferably, the pulse oximeter is placed on the subject's index finger. In one embodiment of the present invention, a pulse oximeter is built-in or hard-wired to the interface box. Alternatively, the pulse oximeter can be a separate unit in communication with either the interface box or the base station via either a wired or wireless connection.

Kinetic data can be obtained by accelerometers placed on the subject. Alternatively, several accelerometers can be placed in various locations on the subject, for example on the wrists, torso, and legs. These accelerometers can provide both motion and general position/orientation data by measuring gravity. A video signal can also provide some kinetic data after processing. Alternatively, stereo video signals can provide three-dimensional position and motion information. Kinetic data includes but is not limited to frequent tossing and turning indicative of an unsuitable mattress, excessive movement of bedding indicating unsuitable sleeping temperatures, and unusual movement patterns indicating pain.

While environmental data isn't as important as with in-home monitoring, environmental data can be collected by video cameras, microphones (to detect noise level, etc.), photodetectors, light meters, thermal sensors, particle detectors, chemical sensors, mold sensors, olfactory sensors, barometers, hygrometers, and the like. Environmental data can provide insight into the subject's sleeping location and habits that is unavailable in the traditional laboratory setting. Environmental data can indicate that the subject's sleeping location is a potential source of the subject's sleeping difficulty. By way of example, but not limitation, environmental data can indicate that the subject's sleeping location has an unsuitable temperature, humidity, light level, noise level, or air quality. For example, these environmental conditions can cause sweating, shivering, sneezing, coughing, noise, and/or motion that disrupts the patient's sleep. The environmental sensors can be placed anywhere in the subject's sleeping location or on the subject, if appropriate. Preferably, the environmental sensors are placed near, but not necessarily on, the subject. Environmental data while not as important for these methods may have some application where the patient or subject is being diagnosed in an environment of long term care, particularly where these environmental factors may continue to affect the patient or subject long after the diagnosis.

Other sensors can be used to measure various parameters of a subject's physiological, kinetic, or environmental conditions. These other parameters are preferably measured using sensors or devices such as a photodetectors, light meters, accelerometers, pneumotachometers, strain gauges, thermal sensors, pH sensors, chemical sensors, transducers, piezo sensors, magnetometers, pressure sensors, static charge-sensitive beds, audio monitors, microphones, reflective markers, video monitors, hygrometers, and the like. Because the system is programmable, potentially any transducer-type sensor that outputs an electrical signal can be used with the system.

Various embodiments of the present invention include the step of connecting the applied sensors to a patient data acquisition system. The sensors can be connected to the patient data acquisition system either before or after they are applied to the subject. As an example of connecting the sensors to the patient data acquisition system after the sensors are applied to the subject, a nurse can apply the sensors to the patient or subject in the patient's room. The nurse or other caretaker can then connect the sensors with leads to the patient data acquisition system. Alternatively, the sensors can be connected to the patient data acquisition system and then applied to the patient, preferably in the patient's room.

The sensors can be permanently hardwired to at least part of the patient data acquisition system. More preferably, the sensors are connected to at least part of the patient data acquisition system via releasable connector. The physiological sensors are generally hardwired (permanently or via releasable connector) to the patient data acquisition system, but the ongoing evolution in wireless sensor technology may allow sensors to contain transmitters. Optionally, such sensors are wirelessly connected to the patient data acquisition system. As such, these sensors and the wireless connection method are considered to be part of the present invention. With the advances in microelectromechanical systems (MEMS) sensor technology, the sensors may have integrated analog amplification, integrated A/D converters, and integrated memory cells for calibration, allowing for some signal conditioning directly on the sensor before transmission.

Preferably, the sensors are all connected in the same way at the same time, although this is certainly not required. It is possible, but less preferable, to connect the sensors with a combination of methods (i.e., hardwired or wireless) at a combination of times (i.e., some before application to the subject, and some after application to the subject or patient).

Preferably, at least two sensors are used to collect patient data; even more preferably, at least four sensors are used to collect patient data; still more preferably, at least six sensors are used to collect patient data; still more preferably, at least eight sensors are used to collect patient data; still more preferably at least ten sensors are used to collect patient data; still more preferably, at least fifteen sensors are used to collect patient data; still more preferably, at least twenty sensors are used to collect patient data; and most preferably, twenty-four sensors are used to collect patient data. Preferably at least one sensor is used to collect environmental data; more preferably, at least two sensors are used to collect environmental data; still more preferably at least four sensors are used to collect environmental data; and most preferably at least six sensors are used to collect environmental data.

Various embodiments of the present invention use a patient data acquisition system. The patient data acquisition system is preferably portable. By portable, it is meant, among other things, that the device is capable of being transported relatively easily. Relative ease in transport means that the device is easily worn and carried, generally in a carrying case, to the point of use or application and then worn by the patient or subject without significantly affecting any range of motion. Furthermore, any components of the patient data acquisition system that are attached to or worn by the subject, such as the sensors and patient interface box, should also be lightweight. Preferably, these patient-contacting components of the device (including the sensors and the patient interface box) weigh less than about 10 lbs., more preferably less than about 7.5 lbs., even more preferably less than about 5 lbs., and most preferably less than about 2.5 lbs. Thus, the patient-contacting components of the device preferably are battery-powered and use a data storage memory card and/or wireless transmission of data, allowing the subject to be untethered. Furthermore, the entire patient data acquisition system (including the patient-contacting components as well as any environmental sensors, base station, or other components) preferably should be relatively lightweight. By relatively lightweight, it is meant preferably the entire patient data acquisition system, including all components such as any processors, computers, video screens, cameras, and the like preferably weigh less in total than about 20 lbs., more preferably less than about 15 lbs., and most preferably less than about 10 lbs. This patient data acquisition system preferably can fit in a reasonably sized carrying case so the patient or assistant can easily transport the system. By being lightweight, wireless and compact, the device should gain greater acceptance for use by the patient or subject.

Various embodiments of the present invention use a patient data acquisition system capable of receiving signals from the sensors applied to the subject and capable of retransmitting the signals or transmitting another signal based at least in part on at least one of the signals. In its simplest form, the patient data acquisition system preferably should interface with the sensors applied to the subject and retransmit the signals from the sensors. Preferably, the patient data acquisition system wirelessly transmits the signals from the sensors. Optionally, the patient data acquisition system also pre-processes the signals from the sensors and transmits the pre-processed signals. Further optionally, the data acquisition is also capable of storing the signals from the sensors and/or any pre-processed signals.

Optionally, the patient data acquisition system can be a single box containing a sensor interface module, a pre-processor module, and a transmitter module. Further optionally, the patient data acquisition system could consist of several boxes that communicate with each other, each box containing one or more modules. For example, the data acquisition could consist of (a) a patient interface box containing a sensor interface module, a pre-processor, a transmitter, and a receiver; and (b) a base station box containing a second pre-processor, a transmitter, and a receiver. In this example, the transmitter and receiver of the patient box are used to communicate with the base station box. The transmitter and receiver of the base station box are used to both communicate with the patient box and a remote monitoring station, remote analysis station, remote data storage station, and the like. Similarly, the data acquisition could consist of (a) a patient interface box containing a sensor interface module, a transmitter, and a receiver; (b) a processor box containing a pre-processor, a transmitter, and a receiver; and (c) a base station box containing only a receiver and a transmitter. In these configurations, it is not necessary for the transmitters to be of the same type. For example, the transmitter in the patient interface box can be a wired or Bluetooth transmitter, and the transmitter in the base station box can be a WiFi or IEEE 802.11 transmitter designed to establish connections over larger distances. The patient data acquisition interface box further is preferably capable of being reprogrammed remotely.

Various embodiments of the present invention use a patient data acquisition system capable of storing and/or retransmitting the signals from the sensors or storing and/or transmitting another signal based at least in part on at least one of the signals. The patient data acquisition system can be programmed and reprogrammed to send all signal data to the removable memory, to transmit all data, or to both transmit all data and send a copy of the data to the removable memory. When the patient data acquisition system is programmed to store a signal or pre-processed signal, the signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc. Preferably, data are stored on removable memory. For both storing and transmitting or retransmitting data, flexible use of removable memory can either buffer signal data or store the data for later transmission. Preferably, nonvolatile removable memory can be used to customize the system's buffering capacity and completely store the data.

In the patient data acquisition system when transmitting the data, the removable memory acts as a buffer. In this situation, if the patient data acquisition system loses its connection with the receiving station, the patient data acquisition system will temporarily store the data in the removable memory until the connection is restored and data transmission can resume and catch up in real time. In the event of a larger transmission failure, the patient data acquisition system can be configured to send all data to the removable memory for storage, then the system does not transmit any information at that time. In this situation, the data stored on the removable memory can be retrieved by either transmission from the patient data acquisition system, or by removing the memory for direct reading.

The method of directly reading will depend on the format of the removable memory. Preferably the removable memory is easily removable and can be removed instantly or almost instantly without tools. The memory is preferably in the form of a card and most preferably in the form of a small easily removable card with an imprint (or upper or lower surface) area of less than about two sq. in. If the removable memory is being used for data storage, preferably it can write data as fast as it is produced by the system, and it possesses enough memory capacity for the duration of the test. These demands will obviously depend on the type of test being conducted, tests requiring more sensors, higher sampling rates, and longer duration of testing will require faster write speeds and larger data capacity. The type of removable memory used can be almost any type that meets the needs of the test being applied. Some examples of the possible types of memory that could be used include but are not limited to Flash Memory such as CompactFlash, SmartMedia, Miniature Card, SD/MMC, Memory Stick, or xD-Picture Card. Alternatively, a portable hard drive, CD-RW burner, DVD-RW burner or other data storage peripheral could be used. Preferably, a SD/MMC—flash memory card is used due to its small size. A PCMCIA card is least preferable because of the size and weight.

When the patient data acquisition system is programmed to retransmit the signals from the sensors, preferably the patient data acquisition system transmits the signals to a processor for analysis. More preferably, the patient data acquisition system immediately retransmits the signals to a processor for analysis. Optionally, the patient data acquisition system receives the signals from one or more of the aforementioned sensors and stores the signals for later transmission and analysis. Optionally, the patient data acquisition system both stores the signals and immediately retransmits the signals.

When the patient data acquisition system is programmed to retransmit the signals from the sensors or transmit a signal based at least in part on the signal from the sensors (collectively "to transmit" in this section), the patient data acquisition system preferably transmits the data through a wireless system, or some combination or a wireless and tethered system. When the system is configured to transmit data, preferably the data transmission step utilizes a two-way (bi-directional) data transmission. Using two-way data transmission significantly increases data integrity. By transmitting redundant information, the receiver (the processor, monitoring station, or the like) can recognize errors and request a renewed transmission of the data. In the presence of excessive transmission problems, such as transmission over excessive distances or obstacles absorbing the signals, the patient data acquisition system can control the data transmission or independently manipulate the data. With control of data transmission it is also possible to control or re-set the parameters of the system, e.g., changing the transmission channel or encryption scheme. For example, if the signal transmitted is superimposed by other sources of interference, the receiving component could secure a flawless transmission by changing the channel. Another example would be if the transmitted signal is too weak, the receiving component could transmit a command to increase the transmitting power. Still another example would be for the receiving component to change the data format of the transmission, e.g., in order to increase the redundant information in the data flow. Increased redundancy allows easier detection and correction of transmission errors. In this way, safe data transmissions are possible even with the poorest transmission qualities. This technique opens a simple way to reduce the transmission power requirements, thereby reducing the energy requirements and providing longer battery life. Another advantage of a bi-directional digital data transmission lies in the possibility of transmitting test codes in order to filter out external interferences, for example, refraction or scatter from the transmission current. In this way, it is possible to reconstruct falsely transmitted data.

Preferably, the patient data acquisition system has a battery life of at least four hours, more preferably of at least eight hours, still more preferably at least twelve hours, even more preferably at least sixteen hours, and most preferably of at least twenty-four hours.

All of the preferable embodiments of the methods of the present invention employ a wireless patient data acquisition system. This wireless patient data acquisition system consists of several components, each wirelessly connected. Data is collected from the sensors described above by a patient interface box. The patient interface box then wirelessly transmits the data preferably to a separate signal pre-processing module, which then wirelessly transmits the pre-processed signal to a receiver. Alternatively, the patient interface box processes the signal and then directly transmits the processed signal directly to a receiver or database using wireless technology. Further alternatively, the patient interface box wirelessly transmits the signals to the receiver, which then pre-processes the signal. Preferably, the wireless technology used by the patient data acquisition system components is radio frequency based. Most preferably, the wireless technology is digital radio frequency based. The signals from the sensors and/or the pre-processed signals are transmitted wirelessly to a receiver, which can be a base station, a transceiver hooked to a computer, a personal digital assistant (PDA), a cellular phone, a wireless network, or the like. Most preferably, the physiological signals are transmitted wirelessly in digital format to a receiver.

Wireless signals between the wireless patient data acquisition system components are both received and transmitted via frequencies preferably less than about 2.0 GHz. More preferably, the frequencies are primarily 902-928 MHz, but Wireless Medical Telemetry Bands (WMTS), 608-614 MHz, 1395-1400 MHz, or 1429-1432 MHz can also be used. The present invention may also use other less preferable frequencies above 2.0 GHz for data transmission, including but not limited to such standards as Bluetooth, WiFi, IEEE 802.11, and the like.

When a component of the wireless patient data acquisition system is configured to wirelessly transmit data, it is preferably capable of conducting a RF sweep to detect an occupied frequency or possible interference. The system is capable of operating in either "manual" or "automatic" mode. In the manual mode, the system conducts an RF sweep and displays the results of the scan to the system monitor. The user of the system can then manually choose which frequency or channel to use for data transmission. In automatic mode, the system conducts a RF sweep and automatically chooses which frequencies to use for data transmission. The system also preferably employs a form of frequency hopping to avoid interference and improve security. The system scans the RF environment then picks a channel over which to transmit based on the amount of interference occurring in the frequency range.

The receiver (base station, remote communication station, or the like) of various embodiments of the wireless patient data acquisition system can be any device known to receive RF transmissions used by those skilled in the art to receive transmissions of data. By way of example but not limitation, the receiver can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the receiver can further transmit data to another device and/or back. Further optionally, two different receivers can be used, one for receiving transmitted data and another for sending data. For example, with the wireless patient data acquisition system used in the present invention, the receiver can be a wireless router that establishes a broadband Internet connection and transmits the physiological signal to a remote Internet site for analysis, preferably by the subject's physician or another clinician. Other examples of a receiver are a PDA, computer, or cell phone that receives the data transmission, optionally re-processes the information, and re-transmits the information via cell towers, land phone lines, or cable to a remote processor or remote monitoring site for analysis. Other examples of a receiver are a computer or processor that receives the data transmission and displays the data or records it on some recording medium that can be displayed or transferred for analysis at a later time.

The preferred embodiment of secure data transmission that is compatible with HIPAA and HCFA guidelines will be implemented using a virtual private network. More preferably, the virtual private network will be implemented using a specialized security appliance, such as the PIX 506E, from Cisco Systems, Inc, capable of implementing IKE and IPSec VPN standards using data encryption techniques such as 168-bit 3DES, 256-bit AES, and the like. Still more preferably, secure transmission will be provided by a $3^{rd}$ party service provider or by the healthcare facility's information technology department. The system will offer configuration management facilities to allow it to adapt to changing guidelines for protecting patient health information (PHI).

Preferably, the patient data acquisition system retransmits the signals from the sensors applied to the subject (or patient) or transmits a signal based at least in part on at least one of the physiological, kinetic, or environmental signals at substantially a same time as the signal is received or generated. At substantially the same time preferably means within approximately one hour. More preferably, at substantially the same time means within thirty minutes. Still more preferably, at substantially the same time means within ten minutes. Still more preferably, at substantially the same time means within approximately one minute. Still more preferably, at substantially the same time means within milliseconds of when the signal is received or generated. Most preferably, a substantially same time means that the signal is transmitted or retransmitted at a nearly instantaneous time as it is received or generated. Transmitting or retransmitting the signal at substantially a same time allows the physician or monitoring service to review the subject's physiological and kinetic signals and the environmental signals and if necessary to make a determination, which could include modifying the patient's treatment protocols or asking the subject (patient) or caregiver to adjust the sensors.

Various embodiments of the present invention include a step of monitoring a patient from a separate monitoring location. Data transmitted in a remote monitoring application may include, but are not limited to, physiological data, kinetic data, environmental data, audio, and/or video recording. It is preferable that both audio and video communications be components of the envisioned system in order to provide interaction between patient and caregiver.

The envisioned remote monitoring step will require data processing, storage, and/or transmission. This step may be completed or accomplished in one or more modules of the patient data acquisition system. The preferred embodiment realizes the remote system as two separate components with a patient interface module that can collect, digitize, store, and transmit data to a base station module that can store, process, compress, encrypt, and transmit data to a remote monitoring location.

Preferably, the data is transmitted from a base station to a database or remote monitoring location with a wireless module or card through a cellular service provider. Also preferably, the data is transmitted from a base station to a database or remote monitoring location through a wireless network or a wired local area network. The envisioned remote monitoring application may allow for multiple remote monitoring locations anywhere in the world. For instance, for an inpatient a nurse in for example a general surgical unit may apply the sensors and then monitor the data for adequate sensor placement while at the same time a remote sleep technician monitors the data for adequate sensor placement and to score the analysis. Remote data collection to monitoring station configurations may include, but are not limited to one-to-one, one-to-many, many-to-one, or many-to-many. The envisioned system may include a central server, or group of servers that can collect data from one or more remote sites and offer delivery to multiple viewing clients.

It is preferable that the remote monitoring application employ a wireless network link between the patient and the sleep unit or laboratory such as a cellular wireless network. Other wireless techniques include but are not limited to satellite communications, direct radio, infrared links, and the like. Data transmission through a wired network such as dial-up modem, digital subscriber line (DSL), or fiber-optic, while less preferable, can also be used. Bandwidth management facilities will be employed to facilitate remote monitoring in low-speed communication networks. Several data compression techniques are envisioned to maximize system utilization in low-bandwidth environments. It is also preferably that the patient or subject is not tethered to any device other than a small, portable patient data acquisition box that can be held or attached easily to the patient or subject.

Data compression using lossless encoding techniques can provide basic throughput optimization, while certain lossy encoding techniques will offer far greater throughput while still providing useful data. Lossy encoding techniques may include but are not limited to decimation, or transmission of a compressed image of the data. The preferred method for encoding will include special processing from the transmitter that will preprocess the data according to user-selectable options, such as digital filtering, and take into the account the desired visual representation of that information, such as pixel height and target image width. Facilities can be made within the system to control the encoding in order to optimize utilization on any given network. Control over the encoding methods may include, but is not limited to selection of a subset of the entire set of signals, target image size, and decimation ratio.

Data encryption can be applied to secure data transmissions over any network. Encryption methods may include but are not limited to simple obfuscation and sophisticated ciphers.

The preferred embodiment of the aforementioned remote monitoring system (a form of the patient data acquisition system) will consist of several system modules. A patient interface module will collect physiological and kinetic data and transmit them to a base station module. The base station module will receive the physiological and kinetic data from the patient module, and will also directly connect to the environmental sensors. The base station module will consist of an embedded computer equipped with a cellular wireless data/voice card and a night-vision video acquisition system. The embedded computer will collect, analyze, compress, and encrypt the data and relay them to one or more viewing caregivers. The remote monitoring systems will broadcast their dynamically assigned IP addresses to a dedicated address server, which will be used for lookup by the viewing caregivers. Computer software used by caregivers will enumerate each remote monitoring system in the field using the aforementioned address server and allow caregivers to select one or more for monitoring. The software will have the ability to control data acquisition including start and stop of acquisition, as well as system reconfiguration.

The software will also provide real-time control over the display of data including page width, amplitude, color, montage, and the like. The software will also provide both real-time video and audio communication with the patient using dual services from the cellular card. Video will preferably be transmitted through the data connection, and audio will preferably be transmitted through the voice connection.

Signal quality of the signals from all the sensors can be affected by the posture and movement of the subject. For methods of the present invention, it is important to reduce motion artifacts from the sensor placement. Errors in the form of noise can occur when biopotential data acquisition is performed on a subject. For example, a motion artifact is noise that is introduced to a biopotential signal via motion of an electrode placed on the skin of a subject. A motion artifact can also be caused by bending of the electrical leads connected to any sensor. The presence of motion artifacts can result in misdiagnosis, prolong procedure duration and can lead to delayed or inappropriate treatment decisions. Thus, it is imperative to remove motion artifact from the biopotential signal to prevent these problems from occurring during treatment.

The present method of collecting signals from a subject includes a method for reducing motion artifacts. Preferably, the electrode sensors are used with conductive gels or adhesives. More preferably, dry electrodes are used with or without conductive gels or adhesives. Still more preferably, the device's firmware and/or software uses body motion information for artifact correction. Most preferably, a combination of the above methods is used.

The most common methods for reducing the effects of motion artifacts in sensors such as electrodes have focused on skin deformation. These methods include removing the upper epidermal layer of the skin by abrasion, puncturing the skin near the electrode, or measuring skin stretch at the electrode site. The methods for skin abrasion ensure good electrical contact between the electrode and the subject's skin. In this method, an abrasive pad is mechanically rotated on the skin to abrade the skin surface before electrode placement. Moreover, medical electrodes have been used with an abrading member to prepare the skin after application of the electrode whereby an applicator gun rotates the abrading member. Methods of skin preparation that abrade the skin with a bundle of fibers have also been disclosed. The methods discussed above provide a light abrasion of the skin to reduce the electrical potential and minimize the impedance of the skin, thereby reducing motion artifacts.

Skin abrasion methods can cause unnecessary subject discomfort, prolong procedure preparation time and can vary based on operator experience. Furthermore, skin abrasions methods can lead to infection, and do not provide an effective solution to long term monitoring. Dry physiological recording electrodes could be used as an alternative to gel electrodes. Dry physiological recording electrodes of the type described in U.S. Pat. No. 7,032,301 are herein incorporated by reference. Dry physiological electrodes do not require any of the skin abrasion techniques mentioned above and are less likely to produce motion artifacts in general.

Although the above-mentioned methods reduce motion artifacts, they do not completely eliminate them. The invention preferably incorporates a step to more completely remove motion and other artifacts by firmware and/or software correction that utilizes information collected preferably from a sensor or device to detect body motion, and more preferably from an accelerometer. In certain embodiments of the present invention, a 3-D accelerometer is directly connected to the patient data acquisition system. The patient data acquisition system receives signal inputs from the accelerometer and at least one set of other physiological or kinetic signals. The microprocessor applies particular tests and algorithms comparing the two signal sets to correct any motion artifacts that have occurred. The processor in one embodiment applies a time synchronization test, which compares the at least one set of physiological or kinetic signal data to the accelerometer signal data synchronized in time to detect motion artifacts and then remove those artifacts. Alternatively, the processor may apply a more complicated frequency analysis. Frequency analysis preferably in the form of wavelet analysis can be applied to the accelerometer and at least one set of physiological or kinetic signals to yield artifact detection. Yet another alternative is to create a neural net model to improve artifact detection and rejection. This allows for the system to be taught over time to detect and correct motion artifacts that typically occur during a test study. The above examples are only examples of possible embodiments of the present invention and are not limitations. The accelerometer data need not be analyzed before wireless transmission; it could be transmitted analyzed by a base station, computer, or the like after transmission. As should be obvious to those skilled in the art, a 2-D accelerometer or an appropriate array of accelerometers could also be used. Gyroscopes could be used as well for these purposes.

Sensors can be used to detect motion of the subject's or patient's body or a portion of their body. The motion information can then be used to detect the posture and movement of the patient or subject and to correct for error in the form of noise or motion artifact in the other sensor channels. To detect motion, various embodiments of the present invention include sensors, devices, and methods of determining the posture and movement of the subject. This information can be used when analyzing the physiological signals. The posture and movement of the subject is preferably determined by signals received from an accelerometer or an array of two or more accelerometers. Accelerometers are known in the art and are suitable for use as motion-monitoring units. Various other types of sensors can be additionally or alternatively used to sense the criteria (e.g., vibration, force, speed, and direction) used in determining motion. For particularly low power designs, the one or more sensors used can be largely mechanical.

Body movement of the subject will result in a high amplitude signal from the accelerometer. The patient data acquisition system can also monitor the sensor signals for any indication that the subject has moved, for example from a supine position to an upright position. For example, the integrated velocity signal computed from the vertical acceleration component of the sensor data can be used to determine that the subject has just stood up from a chair or sat up in bed. A sudden change in the vertical signal, particularly following a prolonged period with little activity while the subject is sleeping or resting, confirms that a posture-changing event occurred.

In addition, a video camera can be used to detect subject movement and position, and the information then used to correct any artifacts that may have arisen from such movement. Preferably, the camera is a digital camera. More preferably, the camera is a wireless digital camera. Still more preferably, the camera is a wireless digital infrared camera. Preferably, the video acquired from the camera is processed so that the subject's movement and position are isolated from other information in the video. The movement and position data that are acquired from the video is then preferably analyzed by software algorithms. This analysis will yield the information needed to make artifact corrections of the physiological signals.

One specific embodiment of the present invention using video patient or subject movement detection involves the use of specially marked electrodes. The electrodes can be any appropriate electrode known in the art. The only change to the electrode is that they preferably have predetermined high contrast marks on them to make them more visible to the video camera. These marking could be manufactured into the electrodes or simply be a sticker that is placed on the back of the electrodes. These markings enable the video system to accurately distinguish the electrodes from the rest of the video image. Using the markers on each visible electrode, the system can calculate of the movement of each individual electrode, thus allowing for more accurate artifact correction.

In another specific embodiment of the invention, the system can detect subject movement by monitoring the actual movement of the patient's or subject's body. Software is applied to the video that first isolates the position of the subject's body, including limbs, and then continues to monitor the motion of the subject.

There are numerous advantages to using video over other means of artifact detection and correction. Foremost, video allows for the calculation of movement artifacts from each individual electrode without the need for accelerometers. This makes the use of video very cost effective in relation to other available methods. The video also can be used in conjunction with the accelerometer data to correct for motion artifacts, thus increasing the precision and accuracy of the system's motion artifact correction capabilities.

Various embodiments of the present invention include the step of pre-processing the signals received from the sensors attached to the patient or subject. The processor or pre-processor of various embodiments of the present invention can be independent, a part of the interface box, or a part of the base station. Optionally, pre-processing can correct artifacts, derive a snore signal, filter a signal, or compress and/or encrypt the data for transmission, each as described above. Preferably, the preprocessing step corrects for artifacts present in the sensor signals.

Various embodiments of the present invention include the step of analyzing the received signals to determine if the patient has a sleeping disorder. This step can be performed or accomplished a number of ways. In one form, a sleep technician or other trained individual scores the sleep test in accordance with Rechtschaffen and Kales (R&K) criteria. Another form uses a standard MSLT analysis. Still another form involves automatic or computer-assisted scoring of the data. The analysis step can include a full R&K score, or specific features can be targeted. For example, in cases of suspected sleep-related breathing disorders, the analysis can focus on detecting and classifying respiratory events. Any analysis method used to diagnose sleeping disorders (including but not limited to insomnia, excessive daytime sleepiness, parasomnias, restless leg syndrome, periodic limb movement disorder, and sleep-disordered breathing such as apneas) based on physiological and/or kinetic data collected while the subject attempts to sleep is an appropriate means of completing this step. Analysis can also include subjective information from the subject, such as the subject's response to questions. Such questions include, but are not limited to, standard subjective questionnaires such as the Epworth and Standford Sleepiness Scale, and asking if the subject slept well.

The analysis can occur after receipt of the entire data set. More preferably, the analysis can take place in near-real time as the data are received. Still more preferably, the analysis is computer-assisted and takes place in near-real time. Alternatively, the data can be partially analyzed, with or without computer assistance, in near-real time, and then fully analyzed at a later time. If at least some of the analysis is conducted in near-real time with computer assistance, the analysis software can provide an alert signal to draw attention to a physiological or technological event. Physiological events include, but are not limited to, changes in blood oxygen saturation, changes in pulse, changes in sleep stage, and subject movement, such as leaving the bed. Technological events include, but are not limited to, movement of a sensor, changes in electrode impedance, or loss of data. Once alerted to a physiological or technological event, the remote monitor can take action, including but not limited to communicating with the subject to address a problem, making a note of the event, conducting more detailed analysis, altering the test parameters, or alerting another individual such as a physician, nurse, sleep technician, or the subject's assistant.

Various embodiments of the present invention include the step of evaluating the received signals to determine if they are adequate for later analysis. This step can be performed or accomplished a number of ways. In the simplest form, the signal can be evaluated once just prior to the start of the sleep study. In another form, the signal is evaluated periodically during the study to determine its quality. Preferably, the signal(s) are evaluated both at the start of the study and periodically during the study. Most preferably, the signals are evaluated at the beginning of the study and continuously during the study. If the signals are evaluated for adequacy, preferably the subject can be contacted to adjust the sensor as necessary. In this way, corrective action can adjust an inadequate signal to increase the value of the sleep study data and enable later analysis. For example with electrodes an impedance check can be performed.

The patient testing in the various embodiments of the present invention is not performed in a sleep unit or laboratory. The result of this is that these methods expand the capabilities of existing sleep units or laboratories. A patient can be testing by an new or existing sleep unit or laboratory at another hospital, at a satellite hospital, at the same hospital but in a different unit, at a nursing home, at a clinic, and the like. Because of the portability and size of the equipment, these methods of sleep analysis can be performed without the need for reconfiguring the room the patient is tested in. Because of the capability of the equipment, this equipment can perform dual purposes or uses such as doing a sleep analysis and EKG simultaneously.

While the equipment used in such methods can be used in a hospital unit adjacent to the sleep unit or laboratory, due to the equipment's robust nature these methods are preferably performed over greater distances. Preferably, the testing location is another hospital, facility, nursing home, clinic or the like. Preferably, the testing location is at least 1 mile from the remote location receiving the data; more preferably, the testing location is at least 5 miles from the remote location receiving the data; even more preferably, the testing location is at least twenty miles from the remote location receiving the data; still more preferably, the testing location is at least fifty miles from the remote location receiving the data; still even more preferably, the testing location is at least two hundred-fifty miles from the remote location receiving the data; more preferably, the testing location is in a different state from the remote location receiving the data; and most preferably, the testing location is in a different country from the remote location receiving the data.

By transmitting the data wirelessly in this application it is meant that the data at least in part of the data transfer process is transmitted wirelessly. This means for example that the data may be transmitted wirelessly from the patient data acquisition box to the base station and then sent via wireless cellular card, internet, through the testing facilities LAN, or any other communication system. This also means for example that the data may be transmitted directly from the patient data acquisition box through a wireless cellular card then over the internet to a database which distributes the data over a hardwired system to the sleep unit or lab. This also means for example that the data may be transmitted directly from the patient data acquisition box with a wireless WWI card directly to a wireless network then over the internet to a processor which retransmits the processed data to the sleep unit or laboratory. Preferably, the patient data acquisition box, however, needs to wirelessly transmit the data. This allows for a simplified patient hookup and improved patient mobility.

The data collected for the sleep analysis conducted under the various methods of the present invention can be viewed by any number of medical personnel and the patient themselves, if appropriate. Preferably, the data is available to a sleep technician, to a doctor making the analysis/diagnosis based on the data, and others involved in these methods. This data can be reviewed at multiple locations including but not limited to the doctor's home or office, or anywhere else the doctor or other individuals associated with the analysis/diagnosis have access to the internet or a intranet.

FIG. 1 is a block diagram of one embodiment of the sleep analysis method of the present invention showing, among other things, the steps of checking the adequacy of signals and communicating with the patient or the patient's caregiver. In this embodiment, a physician, nurse, technician, or the like applies sensors to the patient 4 at a location that is not a sleep unit or laboratory. Before or after the sensors are applied to the patient, they are connected to a wireless data acquisition system 6. The wireless data acquisition system collects some data from the sensors and transmits the data to a remote station 8. At the remote station, a remote monitor checks the signals for adequacy 10. If the signal is not adequate for later analysis 12, the remote monitor communicates with the subject or the subject's caregiver to adjust the sensor 14. After the sensor is adjusted according to instructions from the remote monitor, the wireless data acquisition system collects and transmits more data to the remote monitoring station 8. The signal from the adjusted sensor is checked for adequacy 10. The signal check loop 8, 10, 12, 14 is repeated until the signals from all sensors are adequate for later analysis.

After the wireless data acquisition system is sending adequate signals 12, the sleep test is started by collecting data while the subject attempts to sleep 16. During the test, data is collected and wirelessly transmitted to the remote monitoring station 18. Based on the transmitted data, a sleep analysis is performed and the patient is diagnosed 20.

Figure 2:
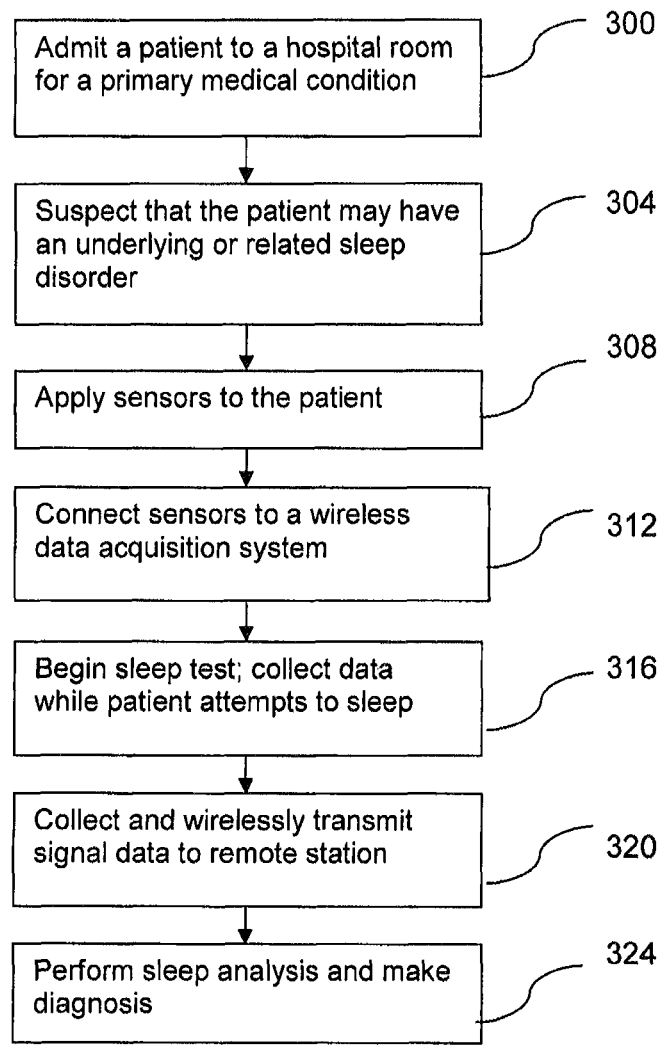
FIG. 2 Block diagram of another embodiment of the present invention.

FIG. 2 is a block diagram of one embodiment of the sleep analysis method of the present invention showing, among other things, the steps of admitting a patient for diagnosis or treatment of another medical condition and suspecting that the patient has a related or underlying sleep disorder. In this embodiment, a patient is admitted to a hospital room that is not primarily used for sleep analysis for a primary medical condition that is not a sleep disorder 300. While the patient is in the hospital, the patient's caregivers suspect that the patient may have an underlying or related sleep disorder 304. A physician, nurse, technician, or the like applies sensors to the patient 308 in the patient's hospital room. Before or after the sensors are applied to the patient, they are connected to a wireless data acquisition system 312. The sleep test is started by collecting data while the subject attempts to sleep in the subject's hospital room 316. During the test, data is collected and wirelessly transmitted to a remote sleep unit or lab or database accessible to a sleep unit or lab 320. Based on the transmitted data, a sleep analysis is performed and the patient is diagnosed 324.

Figure 3:
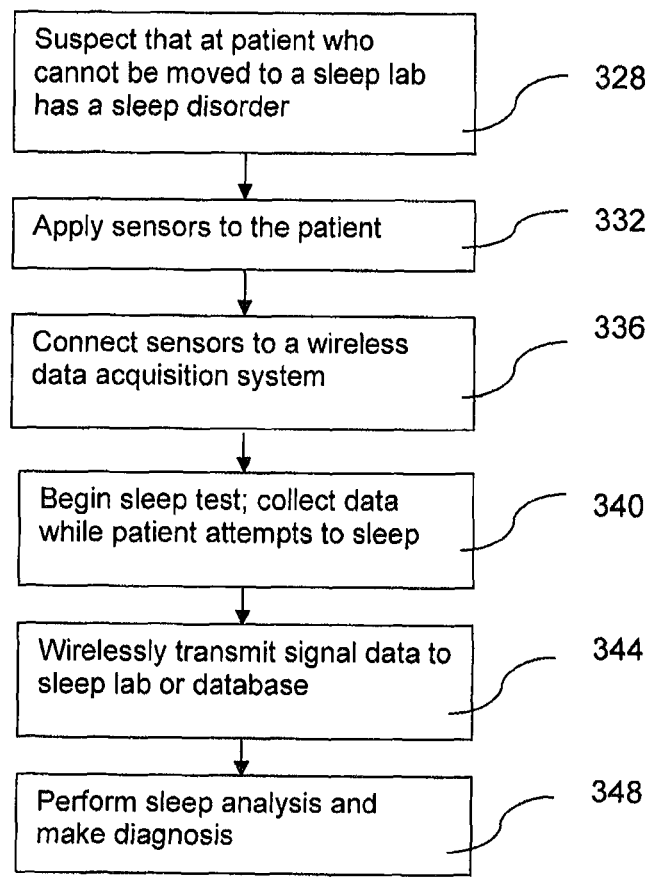
FIG. 3 Block diagram of still another embodiment of the present invention.

FIG. 3 is a block diagram of one embodiment of the sleep analysis method of the present invention showing, among other things, the step of suspecting that a patient who cannot be moved to a sleep lab has a sleep disorder. In this embodiment, a patient cannot be moved to a sleep unit or lab, but the patient's caregiver suspects that the patient has a sleep disorder 328. The patient may be unable to move to a sleep unit or lab for a variety of reasons, including but not limited to a medical condition such as severe cardiovascular disease or paralysis. After the patient's caregiver suspects that the patient has a sleep disorder, a physician, nurse, technician, or the like applies sensors to the subject 332 at the patient's location. Such a location includes a hospital, nursing home, hospice, other skilled nursing facility, or the like. Before or after the sensors are applied to the patient, they are connected to a wireless data acquisition system 336. The sleep test is then started by collecting data while the subject attempts to sleep in the patient's current location 340. During the test, data is collected and wirelessly transmitted to a remote sleep unit or lab, a database accessible to a remote sleep unit or lab, or a remote monitoring station 344. Based on the transmitted data, a sleep analysis is performed and the patient is diagnosed 348.

Figure 4:
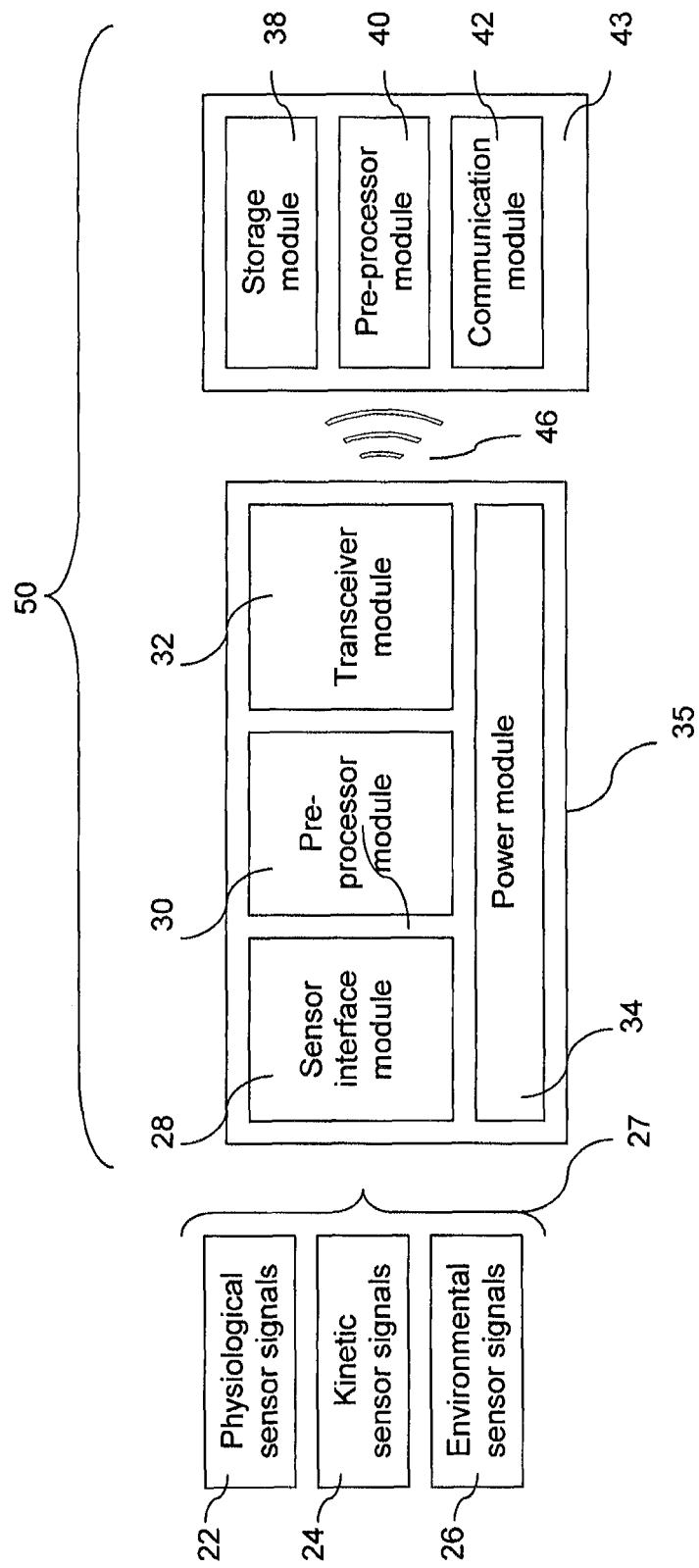
FIG. 4 Signal flow diagram of one embodiment of the present invention showing the patient data acquisition system.

FIG. 4 is a signal flow diagram of one embodiment of the data flow through the wireless data acquisition system used in certain embodiments of the present invention. The sensors generate physiological signals 22, kinetic signals 24, and environmental signals 26. The sensor signals 27 interface with the wireless data acquisition system 50, consisting of (a) a patient interface box 35 containing a sensor interface module 28, a preprocessor module 30, a transceiver module 32, and a power module 34, and (b) a base station 43 containing a storage module 38, a second pre-processor module 40, and a communication module 42. Typically, the patient interface box 35 is worn by the patient during the test period. For portability of the patient interface box 35, the power module 34 can be battery-based. The patient interface box 35 sends data via wireless signal 46 to the base station 43. The base station 43 uses the communication module 42 to wirelessly retransmit the signals from the sensors 27 and/or transmit signals based at least in part on at least one of the signals 27 to remote stations (not shown). Optionally, environmental signals 26 could be fed directly into the base station 43. Further optionally, all the signals 27 could be fed directly into a single box (not shown) containing the sensor interface module 28, pre-processor module 30, storage module 38, communication module 42, and power module 34.

Figure 5:
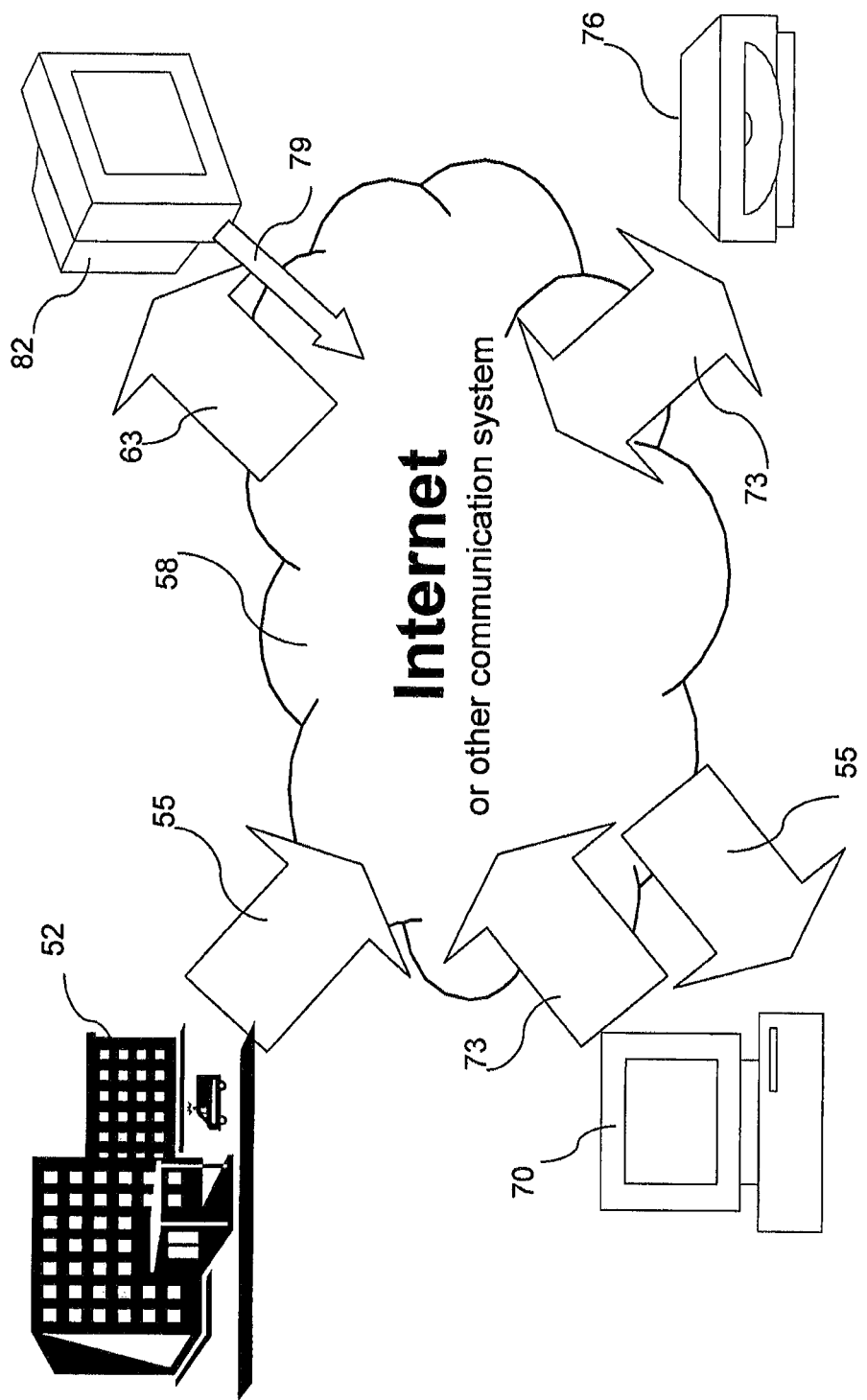
FIG. 5 Schematic representation of one embodiment of the present invention showing the remote data acquisition method.

FIG. 5 is schematic of the remote data acquisition device and system of the present invention. In FIG. 5, a wireless data acquisition system 50 (shown in FIG. 4) is used to receive, filter, and optionally analyze signals 27 (shown in FIG. 4) from sensors (not shown) on a subject (not shown). The wireless in-home data acquisition system 50 transmits a signal based, at least in part, on one or more of the signals from the sensors on the subject. The wireless data acquisition system 50 transmits a signal 55 preferably in real time from the subject's home 52 to a server 70 for analysis. The signal 55 is transmitted over the internet 58 or other communication system such as satellites or other telecommunications system. If the signal 55 is transmitted over the internet 58, preferably the signal 55 is transmitted using a cellular card provided by cellular providers such as for example Sprint, Cingular, AT&T, T-Mobile, Alltel, Verizon or the like. The signal 55 that is transmitted over the internet 58 can be compressed to provide better resolution or greater efficiency. The server 70 performs data analysis (not shown). The analyzed data 73 is then entered into a database 76. The analyzed data 73 in the database 76 is then accessible and can be requested 79 and sent to multiple review stations 82 such as a sleep unit or lab located anywhere in the world for further analysis and review by clinicians, technicians, researchers, doctors and the like.

Figure 6:
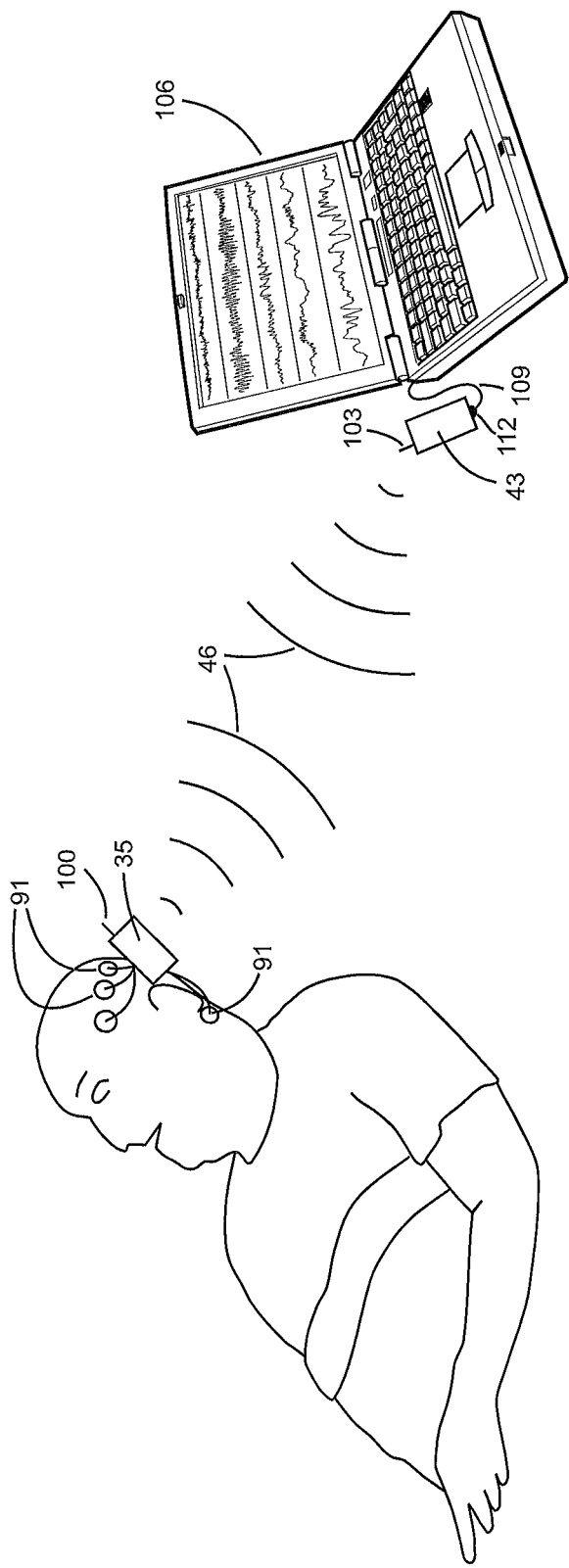
FIG. 6 Schematic representation of one embodiment of the present invention used with a subject to acquire EEG signals from the subject and then transmit them to the receiver and attached computer.

FIG. 6 shows a diagram outlining the wireless data acquisition system in more detail. In FIG. 6, a patient interface box 85 receives signal (not shown) from a sensor 91. This sensor 91 can be an EEG electrode (as shown) or any of the other sensors described herein or known in the art. Although one type of sensor 91 is shown, the patient interface box 85 is capable of accepting multiple signals from multiple sensors 91. In a very simple embodiment of the present invention, the patient interface box 85 generates a wireless signal 94 encoded with data corresponding to the signal from the sensor 91. The patient interface box 85 transmits the wireless signal 94 to base station 97. In FIG. 6, the wireless signal 94 is shown as radio frequency (RF). In this case, the patient interface box 85 generates a radio frequency signal 94 by frequency modulating a frequency carrier and transmits the radio frequency signal through module antenna 100. The base station 97 receives the radio frequency signal 94 through base antenna 103, demodulates the radio frequency signal 94, and decodes the data. It is understood that other wireless means can be utilized with the present invention, such as infrared and optical, for example. RF wireless transmission is preferred. Although one module antenna 100 and one base antenna 103 are shown in this embodiment, it is understood that two or more types of antennas can be used and are included in the present invention. An external programming means 106, shown in FIG. 6 as a personal computer, contains software that is used to program the patient interface box 85 and the base station 97 through data interface cable 109. The data interface cable 109 is connected to the base station 97 by connector 112. Instead of a data interface cable 109, the patient interface box 85 and the base station 97 can be programmed by radio frequency (or other type) of signals transmitted between an external programming means 106 and a base station 97 and the patient interface box 85 or to another base station 97. RF signals, therefore, can be both transmitted and received by both patient interface box 85 and base station 97. In this event the patient interface box 85 also includes a module receiver 133 (shown on FIG. 7) while the base station 97 also includes a base transmitter 84, in effect making both the patient interface box 85 and the base station 97 into transceivers. In addition, the data interface cable 109 also can be used to convey data from the base station 97 to the external programming means 106. If a personal computer is the external programming means 106, it can monitor, analyze, and display the data in addition to its programming functions. The base receiver 80 and module receiver 133 (shown on FIG. 7) can be any appropriate receivers, such as direct or single conversion types. The base receiver 80 preferably is a double conversion superheterodyne receiver while the module receiver 133 (shown on FIG. 7) preferably is a single conversion receiver. Advantageously, the receiver employed will have automatic frequency control to facilitate accurate and consistent tuning of the radio frequency signal 94 received thereby.

Figure 7:
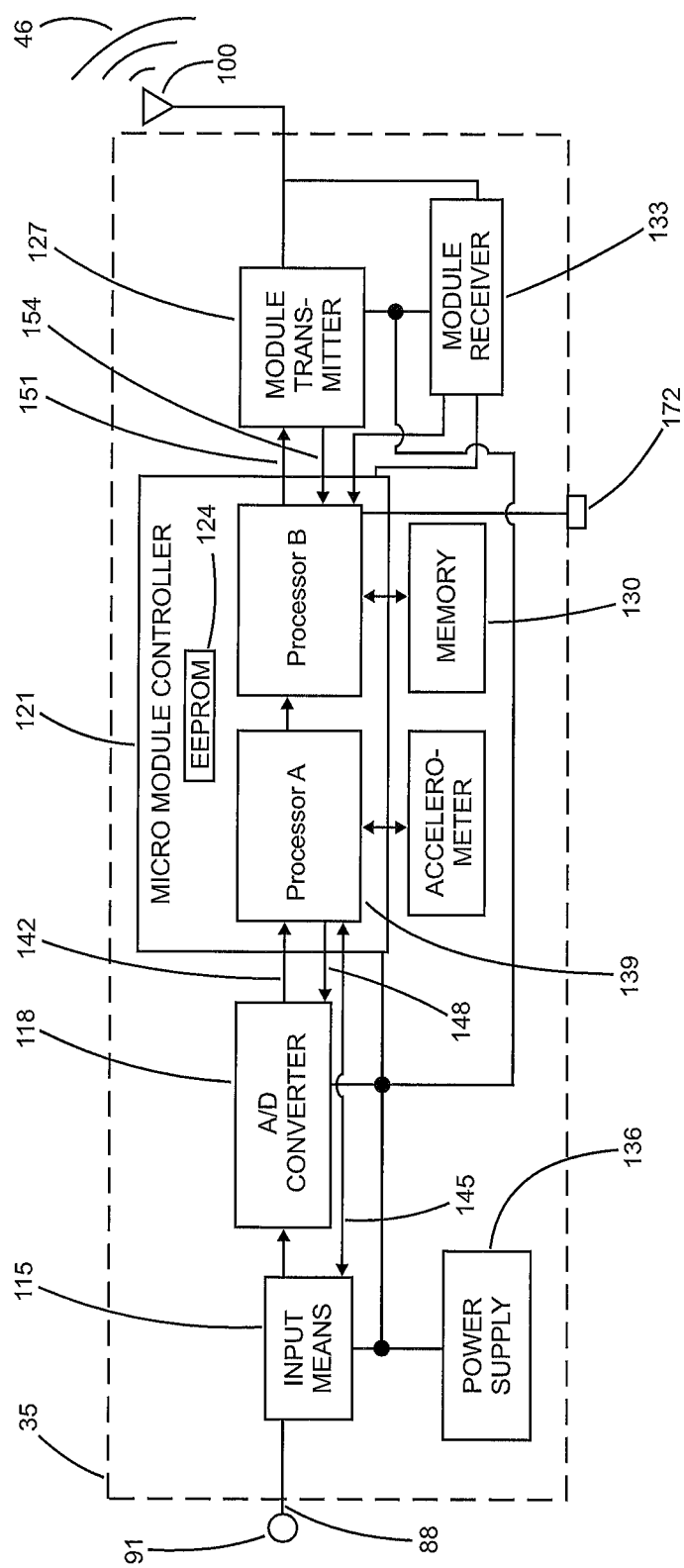
FIG. 7 Block diagram of one embodiment of the signal processing step of the present invention.

Referring now to FIG. 7, there is shown a block diagram of the signal processing module 85 with the sensor 91 and the module antenna 100. The signal processing module 85 comprises input means 115, analog-to-digital (A/D) means 118, a module microcontroller 121 with a nonvolatile memory, advantageously, an EEPROM 124, a module transmitter 127, a connection to removable memory 130, a module receiver 133 and a module power supply 136. Although the module antenna 100 is shown externally located from the signal processing module 85, it can also be incorporated therein. The module antenna 100 may be a printed spiral antenna printed on a circuit board or on the case of the signal processing module 85 or other type of antenna. A module power supply 136 provides electrical power to the signal processing module 85 which includes the input means 115, A/D means 118, module microcontroller 121, module transmitter 127 and module receiver 133. Additionally the signal processing module 85 will preferably contain an accelerometer connected to a microprocessor 139 for position detection, motion detection, and motion artifact correction.

The input means 115 is adjustable either under control of the module microcontroller 121 or by means of individually populatable components based upon the specific external input 88 (i.e. signal from any sensor) characteristics and range enabling the input means 115 to accept that specific external input 88. For example, if the input is a 4-20 mA analog signal, the input means 88 is programmed by the module microcontroller 121 and/or populated with the components needed to accept that range and characteristic of signals. If the input characteristics change the programming and/or components change accordingly but the same platform circuit board design is utilized. In other words, the same platform design is utilized notwithstanding the character, range, or quantity (i.e. number of external inputs 88) [up to a predetermined limit] of the input. For example, bioelectric signals such as EEG, EMG, EKG, EOG, or the like have typical amplitudes of a few microvolts up to a few tens of millivolts. For a given application, a specific frequency band of interest might be from 0.1 Hz to 100 Hz, whereas another application may require measurement of signals from 20 Hz to 10 kHz. Alternatively, measurement of vital signs such as body temperature and respiration rate may deal with signals in a range of +5 volts, with a frequency content from DC (0 Hz) to 20 Hz. For other medical applications, the information of interest may be contained in the signal as a current, current loop sensor, or it may take the form of resistance, impedance, capacitance, inductance, conductivity, or some other parameter. The present invention anticipates using a single device for measuring such widely disparate signal types and presents distinct economic advantages, especially to small enterprises such as a medical clinic located in a rural area, which would be empowered by this invention to conduct tests that would otherwise require the patient travel to a large medical center, with all the attendant cost thereof.

A single system possesses these capabilities due to the selectively adaptable input means 115 and A/D means 118, the frequency-agile module transmitter 127 and base transmitter 116, and the programmable module microcontroller 121 and EEPROM 124. One universal platform design then can be utilized for all applications. In addition, the signal processing module 85 can comprise multiple copies of the input means 115 and the A/D means 118. Cost savings can be achieved by multiplexing at several different points in the input means 115 and the A/D means 118 allowing hardware to be shared among external inputs 88.

After receipt by the input means 115, the external input 88 is inputted to the A/D means 118. The A/D means 118 converts the input to a digital signal 142 and conditions it. The A/D means 118 utilizes at least one programmable A/D converter. This programmable A/D converter may be an AD7714 as manufactured by Analog Devices or similar. Depending upon the application, the input means 115 may also include at least one low noise differential preamp. This preamp may be an INA126 as manufactured by Burr-Brown or similar. The module microcontroller 121 can be programmed to control the input means 115 and the A/D means 118 to provide specific number of external inputs 88, sampling rate, filtering and gain. These parameters are initially configured by programming the module microcontroller 121 to control the input means 115 and the A/D means 118 via input communications line 145 and A/D communications line 148 based upon the input characteristics and the particular application. If different sensors are used, the A/D converter is reconfigured by reprogramming the module microcontroller 121. In this manner, the input means 115 and the A/D means 118 can be configured to accept analog inputs of 4-20 mA, +/−5 volts, +/−15 volts or a range from +/−microvolts to millivolts. They also can be configured to accept digital inputs for digital applications such as detection of contact closure.

The module microcontroller 121 controls the operation of the signal processing module 85. In the present invention, the module microcontroller 121 includes a serial EEPROM 124 but any nonvolatile memory (or volatile memory if the signal processing module remains powered) can be used. The EEPROM 124 can also be a separate component external to the module microcontroller 121. Advantageously, the module microcontroller 121 may be PIC16C74A PIC16C74B or a PIC16C77 both manufactured by MicroChip, or an Amtel AT90S8515 or similar. The module microcontroller may advantageously contain two microprocessors in series as shown in FIG. 7. The module microcontroller 121 is programmed by the external programming means 106 (shown in FIG. 6) through the connector 172 or through radio frequency signal from the base station 97 (shown in FIG. 6). The same module microcontroller 121, therefore, can be utilized for all applications and inputs by programming it for those applications and inputs. If the application or inputs change, the module microcontroller 121 is modified by merely reprogramming. The digital signal 142 is inputted to the module microcontroller 121. The module microcontroller 121 formats the digital signal 142 into a digital data stream 151 encoded with the data from the digital signal 142. The digital data stream 151 is composed of data bytes corresponding to the encoded data and additional data bytes to provide error correction and housekeeping functions. Advantageously, the digital data stream 151 is organized in data packets with the appropriate error correction data bytes coordinated on a per data packet basis. These packets can incorporate data from a single input channel or from several input channels in a single packet, or for some applications may advantageously include several temporally differing measurements of one or a plurality of input channels in a single packet. The digital data stream 151 is used to modulate the carrier frequency generated by the transmitter 127.

The module transmitter 127 is under module microcontroller 121 control. The module transmitter 127 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 151 is used to frequency modulate the carrier frequency resulting in the radio frequency signal 94 which is then transmitted through the module antenna 100. The generation of the carrier frequency is controlled by the module microcontroller 121 through programming in the EEPROM 124, making the module transmitter 127 frequency agile over a broad frequency spectrum. In the United States and Canada a preferred operating band for the carrier frequency is 902 to 928 MHz. The EEPROM 124 can be programmed such that the module microcontroller 121 can instruct the module transmitter 127 to generate a carrier frequency in increments between 902 to 928 MHz. as small as about 5 to 10 kHz. In the US and other countries of the world, the carrier frequency may be in the 902-928 MHz, Wireless Medical Telemetry Bands (WMTS), 608-614 MHz, 1395-1400 MHz, or 1429-1432 MHz or other authorized band. This allows the system to be usable in non-North American applications and provides additional flexibility.

The voltage controlled crystal oscillator (not shown) in the module transmitter 127, not only provides the reference frequency for the module transmitter 127 but, advantageously also provides the clock function 154 for the module microcontroller 121 and the A/D means 118 assuring that all components of the signal processing module 85 are synchronized. An alternate design can use a plurality of reference frequency sources where this arrangement can provide certain advantages such as size or power consumption in the implementation.

The module receiver 133 in the signal processing module 85 receives RF signals from the base station 97 (shown in FIG. 6). The signals from the base station 97 can be used to operate and control the signal processing module 85 by programming and reprogramming the module microprocessor 121 and EEPROM 124 therein.

Figure 8:
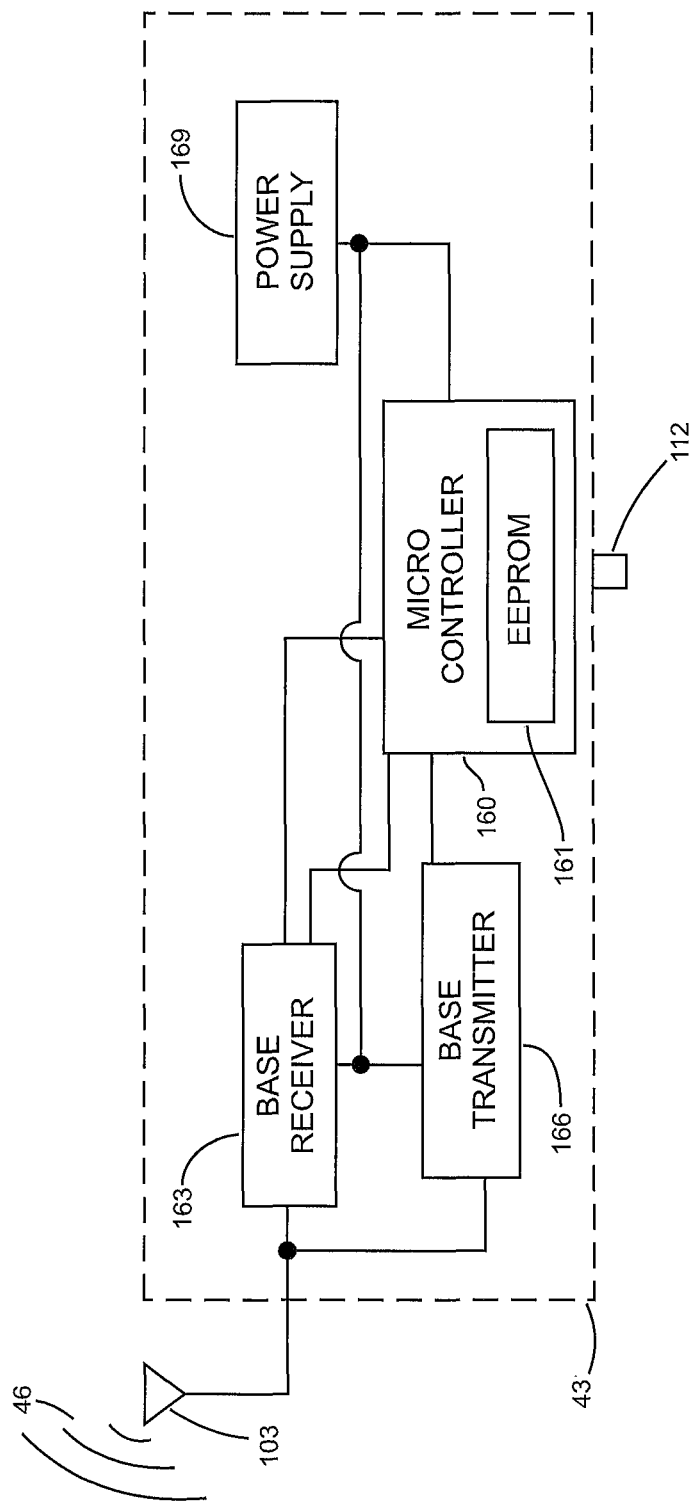
FIG. 8 Block diagram of one embodiment of the base station used in the present invention.

Referring now to FIG. 8, the base station 97 has a base antenna 103 through which RF signals 94 are received. Base microcontroller 160 controls the operation of the base station 97 including base receiver 163, base transmitter 166, and base power supply 169. Base receiver 163 receives the RF signal 94 from base antenna 103. The base receiver 163 demodulates the RF signal 94 and the base microcontroller 160 removes any error correction and performs other housekeeping tasks. The data is then downloaded through connector 112 to the external programming means 106 (shown in FIG. 6) or other personal computer (PC) or data storage/viewing device for viewing in real time, storage, or analysis, or is downloaded to removable memory of some form.

Figure 9:
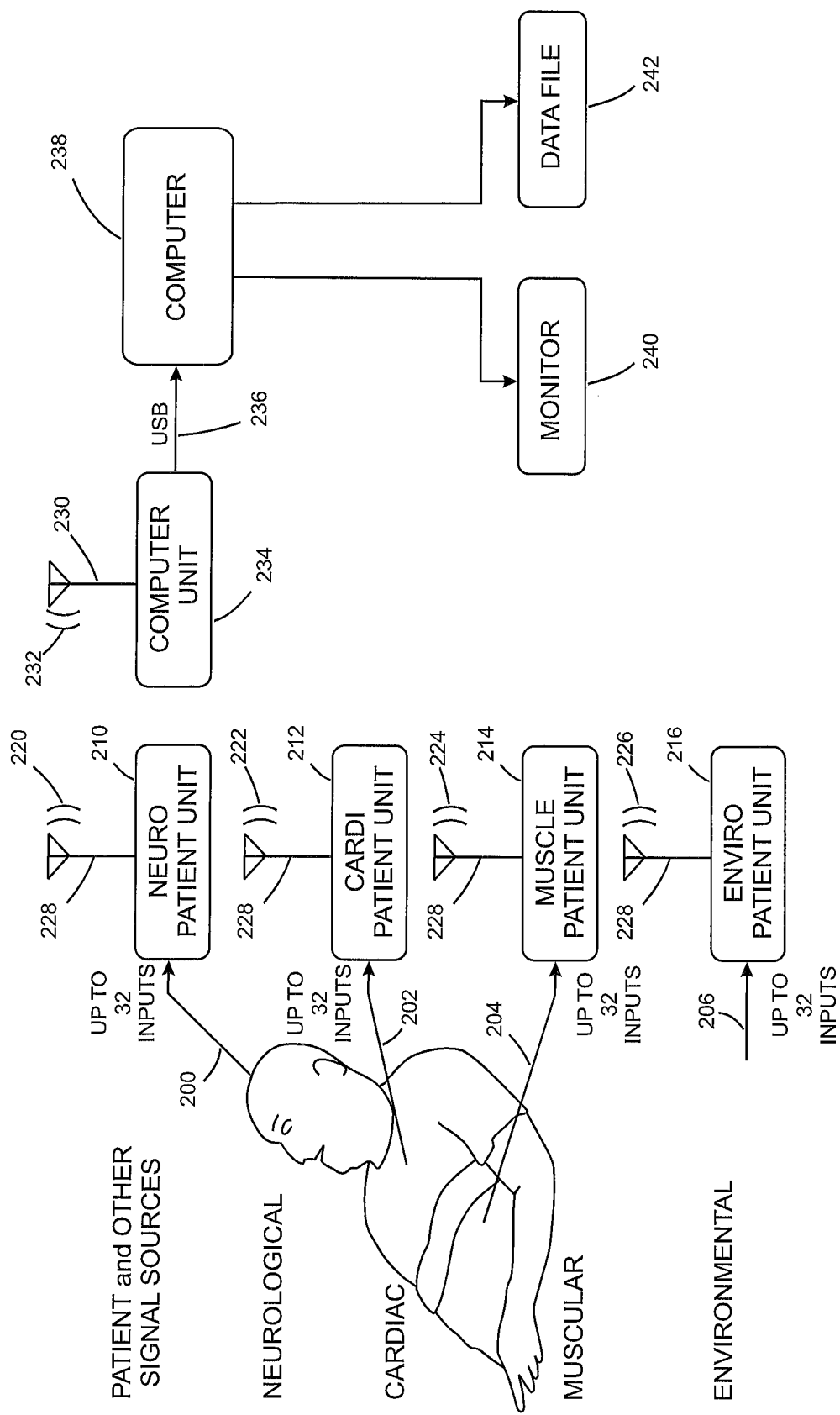
FIG. 9 Schematic representation of one embodiment of the present invention showing an patient data acquisition system of multiple interface boxes used on a single subject, wherein the interface boxes are transmitting to a single receiver.

FIG. 9 is a schematic diagram of a multi-task monitoring system. In FIG. 9, a patient is shown having the neurological 200, cardiac 202, muscular 204, and other environmental conditions 206 measured by sensors (not shown) and input into four separate patient interface boxes 210, 212, 214, and 216. In this example, each unit 210, 212, 214, and 216 can accept up to 32 inputs. The units transmit signals 220, 222, 224, and 226 at different wireless radio frequencies from their respective antennas 228. The signals 220, 222, 224, and 226 do not interfere with each other because they have been manually or automatically selected to reduce interference as described earlier in the application. The signals can be received 232 simultaneously or in some ordered fashion by the antenna 230 on the receiving unit 234. The receiving unit 234 is both data and electrically connected via a USB connection 236 to a main processor or computer 238. The physiological signals are then processed or further processed by the computer 238, depending on whether processing took place in the data acquisition units 210, 212, 214, and 216. The information or data from the computer 238 can be output to a monitor 240 and/or into a data file 242.

Figure 10:
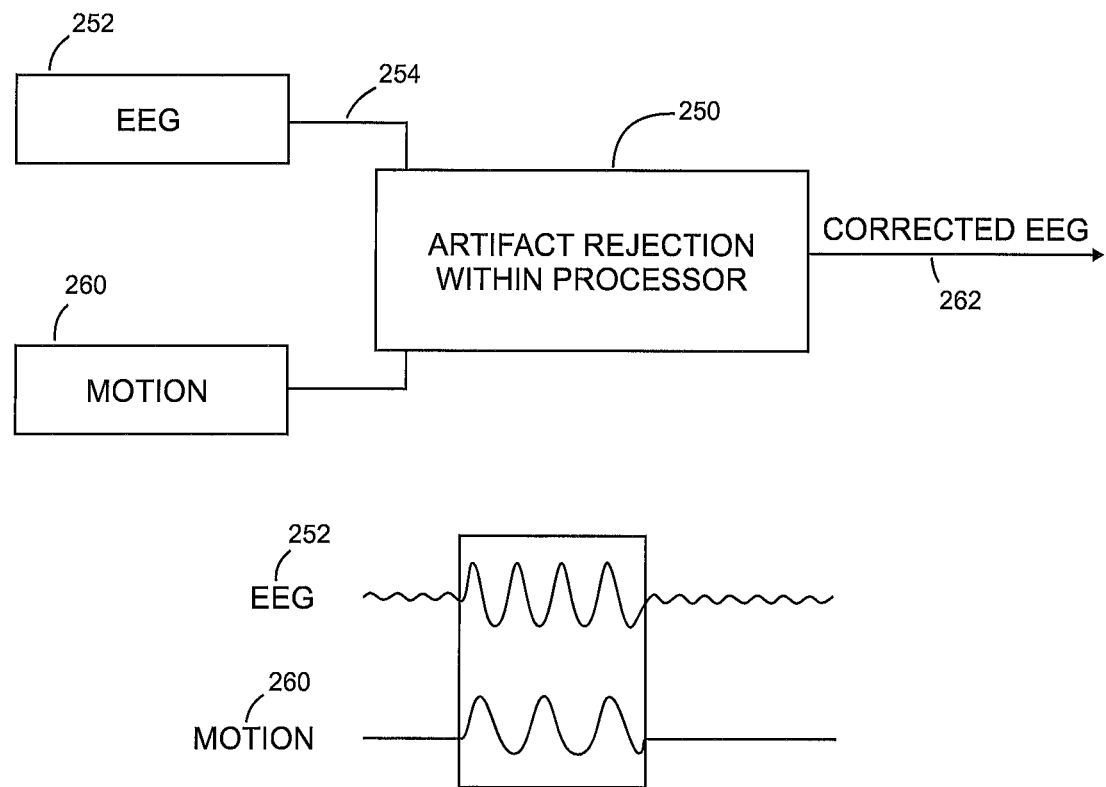
FIG. 10 Block diagram of one embodiment of the present invention showing the motion artifact rejection process.

FIG. 10 is a diagram of an artifact rejection module 250 that can be used in either the in-home data acquisition system (not shown) or a computer or processor (not shown) linked to the data acquisition unit of the present invention. In FIG. 10, a subject's EEG signal 252 is preferably continuously fed 254 into artifact rejection algorithms within the data acquisition unit processor. Simultaneously sensor signals 260 from the subject's movement or motion are also fed into the artifact rejection processor so the EEG signal can be corrected 262 for effects of abnormal or prejudicial motion by the subject. The sensors for determining the subject's motion are described above, but the most preferred is an accelerometer that is incorporated into the EEG data acquisition unit itself.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What we claim is:

1. A sleep diagnostic system for testing multiple subjects comprising:
   a) a database stored on a first non-transitory computer readable medium configured to operate with one or more servers at a first or multiple locations for receiving and transmitting data to and from the database;
   b) a first software stored on a non-transitory computer readable medium and executable by a processor at the first location, a second location and/or the multiple locations configured to process, in part, the data to be stored in the database;
   c) one or more portable, wearable patient interface boxes, each portable, wearable patient interface box adapted to be worn by a subject during testing at a remote sleep location remote from a sleep analysis unit or lab, and the first, the second and the multiple locations, the portable, wearable patient interface box comprising
      i) a battery;
      ii) a nonvolatile digital memory;
      iii) electronics including at least three input channels, which are programmed to receive collected data in real-time from at least three sensors for storage in the nonvolatile digital memory;
      iv) a transceiver or a transmitter adapted to upload the collected data, and/or data based on the collected data to the first software and/or the database; and v) at least two sensor connectors adapted to electrically connect the at least three sensors directly to and/or within the portable, wearable patient interface box;

d) the at least three sensors are selected from a group consisting of: accelerometer(s), fingertip pulse oximeter(s), rip belt(s), respiratory effort belt(s), pressure sensor(s), microphone(s), strain gauge(s), pressure transducer(s), and transducer(s), the at least three sensors adapted i) to be applied to the subject, a first and a second of the at least three sensors adapted to be applied to a finger, wrist, arm and/or torso of the subject;

ii) to measure or derive airflow or snore, respiratory effort, body position, and blood oxygenation of the subject during testing; and iii) to be electrically hardwired and/or releasably connected to the at least three input channels on and/or within the portable, wearable patient interface box adapted to be worn by the subject;

e) the database accessible to individuals from the sleep analysis unit or lab, and adapted to receive the collected data and/or data based on the collected data from the memory of the portable, wearable patient interface box uploaded to the first software and/or the one or more servers associated with the database through the transceiver or the transmitter on the portable, wearable patient interface box;

f) the first software when executed by the processor is configured to automatically identify and quantify physiological events in one or more of the airflow or snore, respiratory effort and blood oxygenation, from the data that was transferred from the portable, wearable patient interface box, the physiological events indicative of a sleeping disorder, the first software further adapted to be executed by a processor at the first location or another processor at a second location both different than the remote sleep location; and g) a communication device adapted to output
i) the respiratory effort and blood oxygenation data from the database,
ii) the identified and quantified physiological events in the data, or
iii) both i) and ii)
in a form adapted so a professional medical diagnosis can be made of whether the patient suffers from a sleep disorder.

2. The sleep diagnostic system in claim 1, wherein a third of the at least three sensors measures airflow and comprises a nasal cannula or a facemask, a first pressure sensor or pressure transducer internal to at least one of the portable, wearable patient interface boxes, and a first air port adapted for connecting the nasal cannula or facemask to the first pressure sensor.

3. The sleep diagnostic system in claim 2, wherein the second sensor measures respiratory effort and comprises a respiratory effort belt, a second pressure sensor or pressure transducer internal to the at least one of the portable, wearable patient interface boxes, and a second air port adapted for connecting the respiratory effort belt to the second pressure sensor or pressure transducer.

4. The sleep diagnostic system in claim 1, wherein the first software further includes an algorithm adapted for identifying changes in sleep stages and calculating a respiratory disturbance index using the collected and transferred data prior to medical diagnosis.

5. The sleep diagnostic system in claim 2, wherein the first software further includes an algorithm adapted for identifying changes in sleep stages and calculating a respiratory disturbance index using the collected and transferred data prior to medical diagnosis.

6. The sleep diagnostic system in claim 3, wherein the first software further includes an algorithm adapted for identifying changes in sleep stages and calculating a respiratory disturbance index using the collected and transferred data prior to medical diagnosis.

7. The sleep diagnostic system in claim 4, wherein the system is adapted to measure or derive heart or pulse rate.

8. The sleep diagnostic system in claim 5, wherein the system is adapted to measure or derive heart or pulse rate.

9. The sleep diagnostic system in claim 6, wherein the system is adapted to measure or derive heart or pulse rate.

10. The sleep diagnostic system in claim 7, wherein the transceiver is further adapted to upload the data from the memory via cellular systems, Internet, satellite, wired-network and/or land lines to the database.

11. The sleep diagnostic system in claim 8, wherein the transceiver is further adapted to upload the data from the memory via cellular systems, Internet, satellite, wired-network and/or land lines to the database.

12. The sleep diagnostic system in claim 9, wherein the transceiver is further adapted to upload the data from the memory via cellular systems, Internet, satellite, wired-network and/or land lines to the database.

13. The sleep diagnostic system in claim 10, further comprising a second software stored on a non-transitory computer readable medium and executable by a processor of a cellular phone of the subject or a care provider, the second software further adapted to allow at least one receiver and/or transceiver of the cellular phone to wirelessly receive the collected data and/or data based on the collected data from the transceiver or transmitter of the portable, wearable patient interface box, and to then transfer the collected data and/or the data based on collected data, to the database via cellular systems, internet, satellite, wired-network and/or land lines to the database.

14. The sleep diagnostic system in claim 11, further comprising a second software stored on a non-transitory computer readable medium and executable by a processor of a cellular phone of the subject or a care provider, the second software further adapted to allow at least one receiver and/or transceiver of the cellular phone to wirelessly receive the collected data and/or data based on the collected data from the transceiver or transmitter of the portable, wearable patient interface box, and to then transfer the collected data and/or the data based on collected data, to the database via cellular systems, internet, satellite, wired-network and/or land lines to the database.

15. The sleep diagnostic system in claim 12, further comprising a second software stored on a non-transitory computer readable medium and executable by a processor of a cellular phone of the subject or a care provider, the second software further adapted to allow at least one receiver and/or transceiver of the cellular phone to wirelessly receive the collected data and/or data based on the collected data from the transceiver or transmitter of the portable, wearable patient interface box, and to then transfer the collected data and/or the data based on collected data, to the database via cellular systems, internet, satellite, wired-network and/or land lines to the database.

16. The sleep diagnostic system in claim 10, wherein movement artifacts caused by a subject movement are removed using the first software and data from the at least three sensors.

17. The sleep diagnostic system in claim 11, wherein movement artifacts caused by a subject movement are removed using the first software and data from the at least three sensors.

18. The sleep diagnostic system in claim 12, wherein movement artifacts caused by a subject movement are removed using the first software and data from the at least three sensors.

19. The sleep diagnostic system in claim 16, wherein the snore is measured and/or derived using a pressure sensor or microphone.

20. The sleep diagnostic system in claim 18, wherein the snore is measured and/or derived using a pressure sensor or microphone.

\* \* \* \* \*